United States Patent [19]

Adams et al.

[11] Patent Number: 5,447,957
[45] Date of Patent: Sep. 5, 1995

[54] ANTI-INFLAMMATORY COMPOUNDS

[75] Inventors: Jerry L. Adams, Wayne; Ralph F. Hall, Villanova; George L. Seibel, Wayne, all of Pa.

[73] Assignee: SmithKline Beecham Corp., Philadelphia, Pa.

[21] Appl. No.: 252,851

[22] Filed: Jun. 2, 1994

[51] Int. Cl.⁶ ............................................. A61K 31/195
[52] U.S. Cl. .................................... 514/564; 514/539; 514/562; 560/34; 560/16; 562/432; 562/439
[58] Field of Search ................... 562/439, 432; 560/34, 560/16; 514/539, 562, 564

[56] References Cited

U.S. PATENT DOCUMENTS 3,933,814  1/1976  Haber .................................. 260/248

Primary Examiner—Jose G. Dees
Assistant Examiner—Samuel Barts
Attorney, Agent, or Firm—Dara L. Dinner; Stephen Venetianer; Edward T. Lentz

[57] ABSTRACT

This invention relates to the novel compounds and pharmaceutical compositions of Formula (I).

This invention also relates to a method of treating or reducing inflammation in a mammal in need thereof, which comprises administering to said mammal an effective amount of a compound or composition of Formula (I).

12 Claims, No Drawings

ANTI-INFLAMMATORY COMPOUNDS

FIELD OF THE INVENTION

This invention relates to pharmaceutical compositions and their use as anti-inflammatory agents in mammals.

BACKGROUND OF THE INVENTION

An early event in the response of most inflammatory cells to immunologic activation and other stimuli is the release of newly formed products (mediators) which alter the function and biochemistry of surrounding cells and tissues. The ensuing biological responses, as well as much of the pathogenesis which is attributed to inflammation and allergy, are thought to be dependent on the effects that these newly-formed mediators have on adjacent cells within the inflammatory region.

In the last 20 years, it has become apparent that lipid mediators are among the most potent and important products which are generated during inflammatory reactions. The synthesis of most lipid mediators is initiated by the specific cleavage of complex phospholipid molecules which contain arachidonate at their sn-2 position. Arachidonic acid is predominantly found in the sn-2 position of phospholipids after redistribution by transacylases and its release by sn-2 acylhydrolases from phospholipids represents the rate-limiting step in the formation of eicosanoids (leukotrienes, prostaglandins and thromboxanes) and other hydroxylated fatty acids. As arachidonic acid is released, it is then converted to oxygenated derivatives by at least two enzymatic systems (lipoxygenase and/or cyclooxygenase). Concomitant with arachidonate release, lysophospholipids are formed. One of these lyso phospholipids, 1-alkyl-2-lyso-sn-glycero-3-phosphocholine, is then acetylated to form platelet-activating factor (PAF). Each of the cell types involved in the inflammatory response produce and secrete a unique subset of lipid mediators. The quantities and nature of the metabolites depend on which enzymes and precursor phospholipid pools are available to inflammatory cells.

Once lipid mediators such as PAF and eicosanoids are formed by the aforementioned pathways, they induce signs and symptoms observed in the pathogenesis of various inflammatory disorders. Indeed, the pathophysiological activity of arachidonic acid (and its metabolites) is well known to those skilled in the art. For example, these mediators have been implicated as having an important role in allergy, asthma, anaphylaxis, adult respiratory distress syndrome, reperfusion injury, inflammatory bowel disease, rheumatoid arthritis, endotoxic shock, and cardiovascular disease. Aalmon et al., Br. Med. Bull (1978) 43:285-296; Piper et al., Ann. NY Acad. Sci. (1991) 629:112-119; Holtzman, Am. Rev. Respir. Dis. (1991) 143:188-203; Snyder, Am. J. Physiol. Cell Physiol. (1990) 259:C697-C708; Prescott et at., J. Biol. Chem. (1990) 265:17381-17384.

Similar to arachidonate products, PAF is a potent proinflammatory mediator produced by a variety of cells. In vitro, PAF stimulates the movement and aggregation of neutrophils and the release therefrom of tissue-damaging enzymes and oxygen radicals. PAF has also been implicated in activation of leukocytes, monocytes, and macrophages. These activities contribute to the actions of PAF as having (pathological) physiological activity in inflammatory and allergic responses. PAF has also been implicated in smooth muscle contraction, pain, edema, hypotensive action, increases in vascular permeability, cardiovascular disorders, asthma, lung edema, endotoxin shock, and adult respiratory distress syndrome. PAF elicits these responses either directly through its own cellular receptor(s) or indirectly by inducing the synthesis of other mediators.

Accordingly, a method which antagonises the production of free arachidonic acid, its metabolites or PAF will have clinical utility in the treatment of a variety of allergic, inflammatory and hypersecretory conditions such as asthma, arthritis, rhinitis, bronchitis and urticaria, as well as reperfusion injury and other disease involving lipid mediators of inflammation. Many published patent applications or issued U.S. patents exist which describe various compounds having utility as PAF or eicosanoid antagonists. Such patents include U.S. Pat. Nos. 4,788,205, 4,801,598, 4,981,860, 4,992,455, 4,983,592, 5,011,847, 5,019,581 and 5,002,941.

Phospholipase $A_2$'s ($PLA_2$ (EC 3.1.1.4)) are responsible for the liberation of arachidonic acid from the sn-2 position of phospholipid. They are thought to play an important role in the pathogenesis of inflammation and possibly in immunological dysfunction, both as a cell associated enzyme as well as an extracellular soluble enzyme. Low molecular weight, mammalian Type II 14 kDa $PLA_2$ has been well characterized and is known to exist in both an extracellular form in inflammatory fluids (Kramer et al., J. Biol. Chem., 264:5768-5775 (1989) and in a cell associated form (Kanda et al., Biochemical and Biophysical Research Communications, 163:42-48 (1989) and has been found in a variety of cells and tissues or extracellularly when released in response to antigenic activators or pro-inflammatory mediators such as Interleukin (IL)-1, IL-6 or tumor necrosis factor (TNF). Its presence in such inflammatory fluids, tissue exudates or serum has therefore implicated Type II-14 kDa-$PLA_2$'s role in inflammation (Vadas, et al., (1985) Life Sci. 36, 579-587; and Seilhamer, et al., (1989) J. Biol. Chem. 264, 5335-5338). Recently, the elevated serum levels of $PLA_2$ activity during an inflammatory insult has been attributed to cytokine induction of acute phase protein release from liver, of which the 14 kDa-$PLA_2$ is suggested to be a part (Crowl, et al., (1991) J. Biol. Chem. 266, 2647-2651). In addition, soluble $PLA_2$ activity is markedly elevated in the serum and synovial fluid of patients with rheumatoid arthritis (Stefanski et al., J. Biochem. 100:1297-303 (1986). Furthermore, increasing serum $PLA_2$ levels have been shown to positively correlate with clinical severity (Bomalaski and Clark, Arthritis and Rheumat. 36:190-198 (1993)). Various inhibitors of $PLA_2$ have been described in publications and in U.S. Patents. See for instance U.S. Pat. Nos. 4,959,357; 4,933,365; 5,208,223; 5,208244; Marshall et at., J. Rheumatology 18:1 (1991); Marshall et al., Phospholipase A2, Ed. Pyu Wong, Plenum Press, New York (1990) pages 169-181; Wilkerson, et al., Eur. J. Med. Chem., 26:667, 1991 and Wilkerson, Antiinflammatory Phospholipase $A_2$ Inhibitors, Drugs of the Future, Vol. 15, No. 2 p 139-148(1990). Accordingly, as $PLA_2$ is important in the liberation of arachidoninc acid from phospholipid and may also play a role in the generation of PAF via lysophospholipid formation, inhibition of such an enzyme would be useful for the treatment of disease sates caused thereby.

There are many novel forms of phospholipase $A_2$'s which have recently been discovered. For the purposes herein, members of the sn-2 acylhydrolase family of PLA$_2$'s are divided into low and high molecular weight enzymes be it from mammalian, or nonmammalian sources. Low molecular weight PLA$_2$'s will generally have a molecular weight in the range of 12,000 to 15,000. High molecular weight will be in the range of 30,000 or 56,000 kDa to 110,000 by SDS electrophoresis analysis.

A high molecular weight, cytosolic 85 kDa PLA$_2$ has been isolated and cloned from the human moncytic cell line, U937 (Clark et al., Proc. Natl. Acad. Sci., 87:7708–7712, 1990). The cell-associated Type II-14 kDa-PLA$_2$ in cell lipid metabolism was thought to be the key rate limiting enzyme in lipid mediator formation, until the recent identification of this cell-associated but structurally distinct 85 kDa sn-2 acylhydrolase, (Clark, et al., supra); and Kramer, et al., (1991) J. Biol. Chem. 266, 5268–5272. Like the Type II-14 kDa enyzme, this enzyme is active at neutral pH and Ca$^{2+}$-dependent, but in contrast exhibits a preference for AA in the sn-2 position of phospholipid substrate and migrates from the cytosol to the membrane in a Ca$^{2+}$-dependent manner and is regulated by phosphorylation (Kramer et al., J. Biol. Chem., 266:5268–5272 (1991). The 85 kDa-PLA$_2$ is also distinct from 14 kDa-PLA$_2$s and Ca$^{2+}$-independent PLA$_2$ as demonstrated by different biochemical characteristics such as stability of the 85 kDa-PLA$_2$ to DTT, instability to heat and the lack of inhibition by a phosphonate phospholipid TSA inhibitor of 14 kDa-PLA$_2$. In addition, 85 kDa-PLA$_2$ has been shown to possess a lysophospholipase A$_1$ activity which is not observed with the 14 kDa-PLA$_2$s. The 85 kDa enzyme is similar to the myocardial Ca$^{2+}$-independent PLA$_2$ (Bomalaski and Clark, Arthritis and Rheumat. 36:190–198 (1993)) in that Ca$^{2+}$is not required for catalysis and DTNB inhibition is observed. However, 85 kDa-PLA$_2$ is not inhibited by the suicide inactivator bromoenol lactone, suggesting that the enzyme is distinct from the myocardial enzyme as well.

These characteristics make the 85 kDa-PLA$_2$ a candidate for participation in the liberation of AA from phospholipid stores for subsequent metabolism to lipid mediators. Both the cytosolic 85 kDa PLA$_2$ and a cell associated Type II 14 kDa PLA$_2$ have been found in the human monocyte, neutrophil and platelet (Marshall and Roshak, Biochem. Cell Biol. 71:331–339 (1993)). As noted above most of the cellular lipid mediators found elevated in a variety of inflammatory fluids are formed in response to non-pancreatic 14 kDa PLA$_2$ action. Since arachidonate-containing phospholipids are the key precursors for a broad range of lipid mediators it would not be surprizing that, inflammatory cells would treat these phospholipids differently than other fatty acid-containing phospholipids. In particular, there are enzymes which control the amount of arachidonate in different phospholipid pools and these enzymes are tightly regulated to maintain arachidonate homeostasis. The movement of arachidonate into and from all phospholipids was originally thought to be exclusively by Coenzyme A-dependent acyl transferase activitites. Holub et al., Adv. Lipid Res., 16:1–125 (1978); Lands et al., In The Enzymes of Biological Membranes, ed. Martonosi, A., pp. 3–85, Plenum Press, New York, 1976. However, it has now been demonstrated that an enzyme, Coenzyme A-independent transcylase (CoA-IT), is involved in the movment of 20 carbon higher unsaturated fatty acids, particularly arachidonate, into particular (1-alkyl- and 1-alkenyl) phospholipid pools. These are the phospholipid pools of arachidonate that are preferentially mobilized during cell activation and utilized for eicosanoid and PAF biosynsthesis, respectively.

CoA-IT has a specificity for certain phospholipids as donor and acceptor molecules. The fatty acid transferred is long chained and unsaturated, and almost exclusively arachidonate. Other fatty acids such as the 16:0, 18:1 or 18:2 are not moved into the sn-2 position of alkyl and 1-alkenyl phospholipid pools by CoA-IT. The specificity of CoA-IT is in direct contrast to many other CoA-dependent acylation activities which acylate a wide variety of lysophospholipids with no selectivity for arachidonate.

Accordingly, as CoA-IT is involved in arachidonic acid and phospholipid metabolism, inhibition of such an enzyme would be useful for the treatment of inflammatory, allergic and hypersecretory conditions or disease states caused thereby. Therefore, a method by which CoA-IT is inhibited will consequently and preferentially decrease the arachidonate content of 1-alkyl- and 1-alkenyl-linked phospholipids and will therefore decrease the production of pro-inflammatory mediators such as free arachidonic acid, prostaglandins, leukotriene and PAF during an inflammatory response.

SUMMARY OF THE INVENTION

This invention relates to the novel compounds of Formula (I) and pharmaceutically acceptable salts thereof. The present invention also provides for a pharmaceutical composition comprising a pharmacuetically acceptable carrier or diluent and a compound of Formula (I), or pharmaceutically acceptable salt thereof.

This invention also relates to a method of treating or reducing inflammation in a mammal in need thereof, which comprises administering to said mammal an effective amount of a compound or composition of Formula (I).

This invention also relates to a method of treating disease or disorders mediated by free arachidonic acid, its metabolites and/or PAF by administering to a patient in need thereof, an effective amount of a compound of Formula (I).

This invention also relates to a method of treating disease or disorders mediated by Phospholipase A2 (PLA$_2$) and/or Coenzyme A independent transacylase (CoA-IT) by administering to a patient in need thereof, an effective amount of a compound or composition of Formula (I).

Compounds of Formula (I) are represented by a structure having the formula:

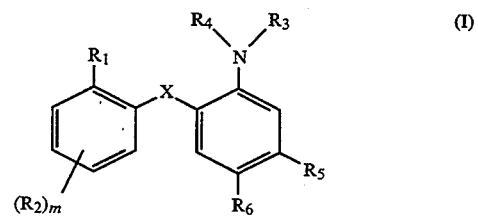

wherein
R$_1$ is (CH$_2$)$_n$OH or (CH$_2$)$_n$CO$_2$R$_8$;
n is 0 or an integer having a value of 1;
X is oxygen or sulfur;
R$_2$ is hydrogen, halogen, optionally substituted C$_{1-8}$ alkyl, or C$_{1-8}$ alkoxy;
m is an integer having a value of 1 or 2;

$R_3$ is $C(O)R_7$;

$R_4$ is hydrogen, or $C_{1-4}$ alkyl;

$R_5$ is hydrogen, halogen, $CF_3$, $CH_3$, $(CH_2)_tC(O)_2R_9$, or $(CH_2)_tOH$;

t is 0 or an integer having a value of 1 or 2;

$R_6$ is hydrogen or halogen;

$R_7$ is $NR_9R_{10}$;

$R_8$ is hydrogen or $C_{1-4}$ alkyl;

$R_9$ is hydrogen or $C_{1-4}$ alkyl;

$R_{10}$ is hydrogen, optionally substituted aryl, optionally substituted aryl$C_{1-2}$ alkyl, optionally substituted $C_{1-8}$ alkyl, or together $R_9$ and $R_{10}$ with the nitrogen to which they are attached form a 5 to 7 membered saturated or unsaturated ring which may optionally comprise an additional heteroatom selected from O/N or sulfur;

or a pharmaceutically acceptable salt thereof.

DETAILED DESCRIPTION OF THE INVENTION

The present invention is directed to a novel method of treating inflammatory disease in a mammal in need thereof by administering to said mammal an effective amount of a compound according to Formula (I). The compounds of Formula (I) may selectively inhibit the $PLA_2$ enzyme, the CoA-IT enzyme or both. Inhibition of either or both, enzymes will result in the treatment of inflammatory occurrences in mammals. Inflammatory states in mammals may include, but are not limited to, allergic and asthmatic manifestations, dermatological diseases, inflammatory diseases, collagen diseases, reperfusion injury and stroke. Treatment of both acute and chronic diseases are possible. Preferred diseases for treatment are arthritis, asthma, allergic rhinitis, inflammatory bowel disease (IBD), psoriasis, reperfusion injury and stroke. For the purposes herein, the compounds of Formula (I) are preferential and selective inhibitors of the low molecular weight $PLA_2$ enzyme.

$R_1$ is suitably $(CH_2)_nOH$ or $(CH_2)_nCO_2R_8$. Preferably $R_1$ is $(CH_2)_nCO_2R_8$ and n is preferably 0. $R_8$ is preferably hydrogen or methyl, more preferably hydrogen, or a pharmaceutically acceptable salt thereof.

Suitably, $R_2$ is independently a substituent on the benzene ring from 1 to 2 times, and such substituent is selected from hydrogen, halogen, an optionally substituted $C_{1-8}$ alkyl, or $C_{1-8}$ alkoxy group Suitably when $R_2$ is halogen it is a chlorine, bromine, fluorine or iodine. When $R_2$ is an optionally substituted $C_{1-8}$ alkyl, the alkyl is substituted one to three times with halogen, such as fluorine, preferably a trifluoromethyl group. The optionally substituted $C_{1-8}$ alkyl moiety if preferably a branched $C_5$ chain, such as 1,1-dimethyl propyl moiety or a $C_8$ branched chain such as 1,1,3,3-tetramethyl butyl moiety.

Suitably X is oxygen or sulfur, preferably oxygen.

Suitably, $R_3$ is $C(O)R_7$ and $R_7$ is the group $NR_9R_{10}$. Suitably $R_9$ is hydrogen or $C_{1-4}$ alkyl; and $R_{10}$ is hydrogen, optionally substituted aryl, optionally substituted aryl$C_{1-2}$ alkyl, optionally substituted $C_{1-8}$ alkyl, or together $R_9$ and $R_{10}$ with the nitrogen to which they are attached form a 5 to 7 membered saturated or unsaturated ring which may optionally comprise an additional heteroatom selected from O/N or sulfur.

Suitably the aryl, aryl alkyl or alkyl moieties of $R_9$ and $R_{10}$ are substituted independently, one to three times, by halogen, trifluoromethyl, aryloxy, methoxy, $CH_2OH$, methyl, or $C(O)2H$. Preferably, the substituents are halogen, or trifluoromethyl. The substituent halogen groups are preferably Cl, Br and fluorine. More preferably the substituents are in the 3,5- position or the 4-position of the aryl ring. Suitably the substituents are 3,5-bis-trifluoromethyl, 3-chloro-4-trifluoromethyl, 4-trifluoromethyl, 4bromo, 4-chloro, or 4-fluoro.

Preferably in the group $NR_9R_{10}$ the $R_9$ group is hydrogen. Preferably when $R_{10}$ is an aryl moiety it is preferably phenyl; when $R_{10}$ is an aryl alkyl moiety it is preferably benzyl; when $R_{10}$ is an alkyl moiety it is preferably a methyl or a $C_8$ unbranched chain. The methyl moiety if substituted is preferably substituted by fluorine to yield a trifluoromethyl group. More preferably $R_9$ is hydrogen. More preferably $R_{10}$ is an optionally substituted phenyl as defined above.

Suitably $R_4$ is hydrogen, or $C_{1-4}$ alkyl, preferably hydrogen.

Suitably $R_5$ is hydrogen, halogen, $CF_3$, $CH_3, CH_2C(O)_2R_9$, or $CH_2OH$, wherein t is 1. Preferably when $R_5$ is $CH_2C(O)_2R_9$, $R_9$ is a $C_{1-4}$ alkyl, preferably t-butyl. Preferred $R_5$ groups are hydrogen, $CF_3$, or halogen. More preferably $R_5$ is hydrogen or $CF_3$.

Suitably $R_6$ is hydrogen or halogen; preferably hydrogen. If $R_6$ is halogen it is preferably fluorine or chlorine.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be foraged with a pharmaceutically acceptable cation, for instance, if a substituent $R_1$ comprises a carboxy group. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo;

"$C_{1-8}$ alkyl" or "alkyl"—both straight and branched chain radicals of 1 to 8 carbon atoms, unless the chain length is otherwise limited, including, but not limited to, methyl, ethyl, n-propyl, iso-propyl, n-butyl, sec-butyl, iso-butyl, tert-butyl, and the like;

"aryl"—phenyl and naphthyl;

"heteroaryl" (on its own or in any combination, such as "heteroaryloxy")—a 5-10 membered aromatic ring system in which one or more rings contain one or more heteroatoms selected from the group consisting of N, O or S, such as, but not limited, to pyrrole, quinoline, isoquinoline, pyridine, pyrimidine, oxazole, thiazole, thiadiazole, triazole, imidazole, or benzimidazole;

"heterocyclic" (on its own or in any combination, such as "heterocyclylalkyl")—a saturated or wholly or partially unsaturated 4-10 membered ring system in which one or more rings contain one or more heteroatoms selected from the group consisting of N, O, or S; such as, but not limited to, pyrrolidine, piperidine, piperazine, morpholine, imidazolidine or pyrazolidine.

"heteroarylalkyl", "aryl alkyl", or "heterocyclic alkyl" is a heteroaryl, aryl or heterocyclic moiety as defined above connected to a $C_{1-4}$ alkyl as defined above unless otherwise indicated, such as but not limited to, benzyl, or phenethyl.

The compounds of the present invention may contain one or more asymmetric carbon atoms and may exist in racemic and optically active forms. All of these compounds are included within the scope of the present invention.

Specifically exemplified compounds of Formula (I) are:

2-[2-[3-[3,5-Bis(trifluoromethyl)phenyl]ureido]-4-triflouro-methylphenoxy]benzoic acid
Methyl 2-[2-[3-[3,5-bis(Trifluoromethyl)phenyl]ureido]-4-trifluoromethylphenoxy]benzoate
2-[2-[3-[3,5-Bis(trifluoromethyl)phenyl]ureido]phenoxy]benzoic acid
2-[2-[3-[3,5-Bis(trifluoromethyl)phenyl]ureido]-4-(trifluoromethyl)-phenoxy]-5-(1,1,3,3-tetramethylbutyl)-benzoic acid
2-[2-[3-(4-Bromophenyl)ureido]-4-trifluoromethylphenoxy]benzoic acid
2-[2-(Nonanamido)phenoxy]benzoic acid
2-[2-[3-[3,5-bis(trifluoromethyl)phenyl]ureido]-4-trifluoromethyl-phenoxy]-5-(1,1-dimethylpropyl)benzoic acid
2-[2-[3-(Octyl)ureido]phenoxy]benzoic acid
2-[2-[3-(Octyl)ureido]-4-trifluoromethylphenoxy]benzoic acid
2-[2-[3,5-Bis(trifluoromethyl)]benzamido-4-trifluoromethylphenoxy]benzoic acid
2-[2-[3-[3,5-Bis(trifluoromethyl)phenyl]ureido-4-trifluoromethyl-Phenoxy]-4-methoxybenzoic acid
2-[2-[3-[3,5-Bis(trifluoromethyl)phenyl]ureido]-4-chlorophenyl]-anthranilic acid
2-[2-[3-(4-Chlorophenyl)ureido]phenoxy]benzoic acid
2-[2-[3-[4-Chloro-3-(trifluoromethyl)phenyl]ureido]phenoxy]benzoic acid Compounds of Formula (I) may be prepared by a process which comprises reacting a suitably protected compound of Formula (2), which are generally commercially available and $R_1$, $R_2$, m are as defined in Formula (I):

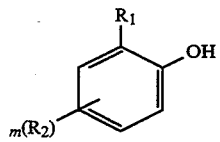
(2)

with a compound of Formula (3) wherein $R_9$ is F, Cl, Br or I, and $R_5$ and $R_6$ are as in, Formula (I):

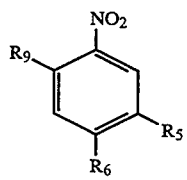
(3)

in a suitable solvent such as dimethylformamide and in the presence of a suitable base such as potassium carbonate with or without added copper at a temperature of 25°–175° C. to provide a compound of Formula (4). In cases where compounds of Formula (2) are not commercially available, such as in some cases when $R_1$ is $RCO_2R_8$, the desired compounds of formula (2) may be prepared by following the procedure of Schmitt et al., *Synthesis*, 1984, 758–760 whose disclosure is incorporated by reference herein.

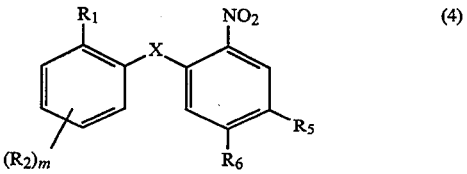
(4)

Reduction of compound (4) with a suitable reducing agent such as iron in a solvent such as acetic acid/ethanol/water, or titanium trichloride in acetic acid water, or $H_2$ in the presence of a catalyst such as palladium on carbon in a solvent such as ethyl acetate or methanol, provides a compound of Formula (5).

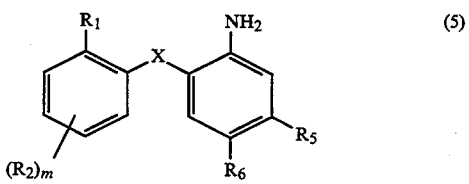
(5)

Reaction of compound (5) with an isocyanate in a suitable solvent such as pyridine provides a compound of Formula (6) wherein $R_4$ is hydrogen and $R_7$ is as defined in Formula (I).

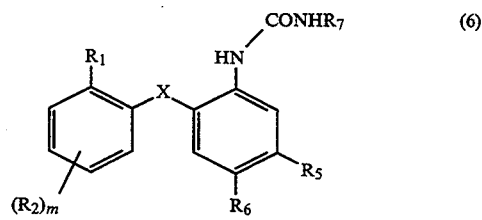
(6)

Reaction of a compound of Formula (5) with a carboxylic acid halide in a suitable solvent such as methylene chloride or pyridine, in the presencd of a suitable base such as pyridine, provides a compound of Formula (7).

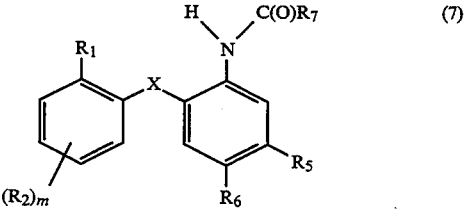
(7)

Compounds of Formula (I) wherein $R_1$ is $(CH_2)_n OH$ may be prepared from compounds of Formula (I) wherein $R_8$ is hydrogen by reaction with a suitable reducing agent such as borane in a suitable solvent such as tetrahydrofuran.

Deprotection (if required) of a compound of Formulas (6–7) and/or conversion to suitable salt forms provides a final compound of Formula (I).

Without further elaboration, it is believed that one skilled in the art can, using procedures analagous to those described herein, utilize the present invention to its fullest extent. The invention will now be described by reference to the following examples which are merely illustrative and are not to be construed as a limitation of the scope of the present invention.

SYNTHETIC CHEMISTRY

Temperatures are recorded in degrees centigrade unless otherwise noted.

EXAMPLE 1

Preparation of 2-[2-[3-(4-Bromophenyl)ureido]-4-(trifluoromethyl)-phenoxy]benzoic acid a) Methyl 2-(2-nitro-4-trifluoromethylphenoxy)benzoate A mixture of methyl salicylate (15.2 g, 0.1 mol), 4-chloro-3-nitrobenzotrifluoride (22.6 g, 0.1 mol), and potassium carbonate (8.3 g, 0.06 mol) in dimethylformamide (100 mL) was stirred under argon and heated in an oil bath to 150° C. for 70 min. The reaction mixture was diluted with ethyl acetate (300 mL), filtered, and the residue washed with ethyl acetate. The combined filtrates were evaporated, and the crude product was purified by flash chromatography (silica gel, ethyl acetate/hexane) to give the title compound as a pale yellow solid; mp 69°–70° C.

b) Methyl 2-(2-amino-4-trifluoromethylphenoxy)benzoate

A mixture of methyl 2-(2-nitro-4-trifluoromethylphenoxy)benzoate (26 g, 0.076 mol) and 10% palladium on carbon (1 g) in ethyl acetate (400 mL) was hydrogenated in a parr bottle at 55 psi for 2 h. The reaction mixture was flushed with argon, filtered through Celite® and evaporated. The crude product was purified by flash chromatography (silica gel, ethyl acetate/hexane) to give the title compound as a white solid. $^1$H NMR (250 MHz, CDCl$_3$) δ7.91 (dd, 1H), 7.45–7.53 (m, 1H), 7.17–7.24 (m, 1H), 6.88–7.03 (m, 3H), 6.78 (d, 1H), 4.25 (br s, 2H), 3.84 (s, 3H).

c) 2-(2-Amino-4-trifluoromethylphenoxy)benzoic acid

A mixture of methyl 2-(2-amino-4-trifluoromethylphenoxy)benzoate (19.2 g, 0.062 mol) and 2N sodium hydroxide (65 mL, 0.13 mol) in tetrahydrofuran (100 mL) was warmed to 50° C. while stirring under argon for 3 h. The tetrahydrofuran was evaporated, and the aqueous solution was acidified with dilute HCl, extracted with ethyl acetate, dried over anhydrous MgSO$_4$, filtered and evaporated. The crude product was recrystallized from EtOAc/hexane to give the title compound as a white crystalline solid. $^1$H NMR (250 MHz, CD$_3$OD) δ7.91 (d, 1H), 7.50 (dd, 1H), 7.22 (dd, 1H), 7.11 (d, 1H), 6.97 (d, 1H), 6.86 (d, 1H), 6.78 (d, 1H).

d) Benzhydrol 2-(2-amino-4-trifluoromethylphenoxy)benzoate

A mixture of 2-(2-amino-4-trifluoromethylphenoxy)benzoic acid (5 g, 0.017 mol) in EtOAc (50 mL) was stirred under argon at 50° C. A solution of diphenyldiazomethane, (3.3 g, 0.017 mol) dissolved in toluene (50 mL) was added dropwise. The solvents were evaporated and the residue was purified by flash chromatography (silica gel, ethyl acetate/hexane) to give the title compound as a viscous oil. $^1$H NMR (250 MHz, CDCl$_3$) δ8.02 (dd, 1H), 7.45–7.52 (m, 1H), 7.20–7.33 (m, 11H), 7.07 (s, 1H), 6.96–7.07 (m, 2H), 6.86–6.91 (m, 1H), 6.73 (d, 1H), 4.00 (br s, 2H).

e) Benzhydrol 2-[2-[3,5-bis (trifluoromethyl)phenylsulfonamido]-4-trifluoromethylphenoxy]benzoate Benzhydrol 2-(2-amino-4-trifluoromethylphenoxy)benzoate (4 g, 8.6 mmol) was dissolved in pyridine (25 mL) and stirred under argon at room temperature. 4-bromophenyl isocyanate (4.05 g, 12.9 mmol) was added in portions, and the mixture stirred for 16 h. The solvent was evaporated, and the residue was purified by flash chromatography (silica gel, ethyl acetate/hexane) to give the title compound as a white solid. mp 194°–195° C.

b) 2-[2-[3-(4-Bromophenyl)ureido]-4-(trifluoromethyl)-phenoxy]benzoic acid

Benzhydrol 2-[2-[3-(4-bromophenyl)ureido]-4-(trifluoromethyl)-phenoxy]benzoate (3.7 g, 5 mmol) was dissolved in ethyl acetate (125 mL) and was hydrogenated for 0.75 hour at 50 psi over 10% palladium on carbon (0.5 g). The catalyst was filtered off and the solvent evaporated to give the crude product which was purified by flash chromatography (silica gel, ethyl acetate/hexane/formic acid). Recrystallization from ethyl acetate/hexane gave the title compound as a white crystalline solid; mp 229°–231° C.

EXAMPLE 2

Preparation of 2-[2-[3-[3,5-Bis (trifluoromethyl)phenyl]ureido]phenoxy]benzoic acid a) Methyl 2-(2-nitrophenoxy)benzoate Methyl salicylate (1.7 mL, 0.0131 mol), 1-chloro-2-nitrobenzene (2.30 mL, 0.01965 mol) and potassium carbonate (3.62 g, 0.0262 mol) were mixed in dimethylformamide (35 mL), under argon, at 150° C. for 16 h. The solvent was evaporated and the crude material was flash chromatographed (silica gel, ethyl acetate/hexane). Concentration in vacuo yielded the title compound. $^1$H NMR (250 MHz, CDCl$_3$) δ8.0 (m, 4H), 7.58 (m, 1H), 7.35 (m, 1H), 7.23 (m, 1H), 7.13 (dd, 1H), 6.85 (dd, 2H).

b) Methyl 2-(2-aminophenoxy)benzoate

Methyl 2-(2-nitrophenoxy)benzoate (540 mg, 0.00198 mol) was dissolved in ethyl acetate (20 mL) and palladium on carbon catalyst (270 mg) was added. The mixture was hydrogenated at 57 psi for 2 h. The catalyst was filtered and the solvents were evaporated to yield the title compound. $^1$H NMR (250 MHz, CDCl$_3$) δ7.83 (dd, 1H), 7.41 (m, 1H), 7.10 (m, 1H), 6.97 (m, 2H), 6.82 (m, 2H), 6.69 (m, 1H).

c) 2-(2-aminophenoxy)-1-benzoic acid

Methyl 2-(2-aminophenoxy)benzoate (430 mg, 0.0018 mol) was mixed in tetrahyrofuran (10 mL) at 5° C. Sodium hydroxide (5 mL) was added dropwise and stirring continued at 5° C. for 10 min. The mixture was then brought to room temperature and stirred for two hours. The solvent was evaporated and water (10 mL) was added to the residue. 3N hydrochloric acid was added to pH 4.0. The aqueous phase was extracted with ethyl acetate to yield the title compound.

d) 2-[2-[3-[3,5-bis(trifluoromethyl)phenyl]ureido]-phenoxy]benzoic acid.

2-(2-aminophenoxy)-1-benzoic acid (180 mg, 0.00079 mol) and 3,5bis(trifluoromethyl)phenyl isocyanate (198 μL, 0.00118 mol) were mixed in pyridine (8 mL), under argon for 16 h. The pyridine was evaporated and the crude product was flash chromatographed (silica gel, methylene chloride/isopropanol/ammonium hydroxide). The solvent was evaporated and the residue was mixed in water and acidified with 3N hydrochloric acid to pH 4.0. The aqueous was extracted with ethyl acetate. The organic phase was dried (MgSO$_4$) and the solvent evaporated to yield the title compound. $^1$H NMR (250 MHz, CD$_3$OD) δ8.20 (q, 1H), 8.00 (s, 2H), 7.95 (q, 1H), 7.50 (m, 2H), 7.20 (m, 2H), 7.00 (m, 2H), 6.85 (q, 1H), 2.05 (s, 1H).

EXAMPLE 3

Preparation of 2-[2-[3-[3,5-Bis (Trifluoromethyl)phenyl]ureido]-4-chlorophenylanthranilic acid a) 2-[2-[3-[3,5-Bis(trifluoromethyl)phenyl]ureido]-4-chlorophenyl]anthranilic acid N-(2-amino-4-chlorophenyl)anthranilic acid (1.09 g, 0.0038 mol), (purchased from Aldrich), was mixed at 0° C., in pyridine, under argon. 3,5-Bis(trifluoromethyl-phenyl)isocyanate was added dropwise to the cold mixture and stirred, under argon for 6 h. The solvent was evaporated and the residue flash chromatographed (silica gel, ethyl acetate/hexane/formic acid). Recrystallization from ethyl acetate/hexane gave the title compound as a white solid. MS (DCI/NH$_3$) m/e 518 [M+H]$^+$.

EXAMPLE 4

Preparation of 2-[2-[3-[3,5-Bis (trifluoromethyl)phenyl]ureido]-4-trifluoromethyl-phenoxy]-5-(1,1,3,3-tetramethylbutyl)benzoic acid a) Methyl 2-hydroxy-5-(1,1,3,3-tetramethylbutyl)benzoate Tertiary-octysalicylic acid (500 mg, 0.0020 mol) was dissolved in ether and methylated with diazomethane to yield the title compound.

b) Methyl 2-(2-nitro-4-trifluoromethylphenoxy)-5-(1,1,3,3-tetramethylbutyl)benzoate Methyl 2-hydroxy-5-(1,1,3,3-tetramethylbutyl)benzoate (520 mg, 0.002 mol), 4-chloro-3-nitrobenzotrifluoride (442 μL, 0.003 mol) and potassium carbonate were mixed in dimethylformamide (20 mL) at 150° C., under argon, for 16 h. The mixture was filtered, the solvent was evaporated and the residue flash chromatographed (silica gel, ethyl acetate/hexane) to yield the title compound. $^1$H NMR (250 MHz, (CD$_3$)$_2$SO) δ8.38 (d, 1H), 7.98 (d, 1H), 7.89 (dd, 1H), 7.78 (dd, 1H), 7.28 (d, 1H), 6.87 (d, 1H) 3.65 (s, 3H), 3.29 (s, 2H), 1.79 (s, 3H), 1.38 (s, 6H), 0.68 (s, 6H).

c) Methyl 2-(2-nitro-4-trifluoromethylphenoxy)-5-(1,1,3,3-tetramethylbutyl)benzoate Methyl-2-(2-nitro-4-trifluoromethylphenoxy)-5-(1,1,3,3-tetramethylbutyl)benzoate (330 mg, 0.0007 mol) was dissolved in ethyl acetate (20 mL) and palladium on carbon catylyst (165 mg) was added under argon. The mixture was hydrogenated in a parr bottle at 59 psi for 16 h to yield the title compound. $^1$H NMR (250 MHz, CD$_3$OD) δ7.94 (d, 1H), 7.55 (dd, 1H), 7.09 (d, 1H), 6.95 (d, 1H), 6.86 (dd, 1H), 6.65 (d, 1H), 1.78 (s, 2H), 1.48 (s, 6H), 0.70 (s, 9H).

d) 2-(2-amino-4-trifluoromethylphenoxy)-5-(1,1,3,3-tetramethylbutyl)benzoic acid Methyl-2-(2-amino-4-trifluoromethylphenoxy)-5-(1,1,3,3-tetramethylbutyl)benzoate (330 mg, 0.0008 mol) was mixed in tetrahyrofuran (15 mL) and cooled to 0° C. 1N Sodium hydroxide was added and stirring was continued, allowing the mixture to warm to room temperature. After 16 h the tetrahydrofuran was evaporated and the residue mixed in water. 3N Hydrochloric acid was added, bringing the pH to 4.0. The aqueous phase was extracted with ethyl acetate. The organic phase was dried (MgSO$_4$) and the solvent was evaporated. The residue was flash chromatographed (silica gel, ethyl acetate/hexane) to yield the title compound. $^1$H NMR (250 MHz, CD$_3$OD) δ7.97 (d, 1H), 7.54 (dd, 1H), 7.09 (d, 1H), 6.71–6.98 (m, 2H), 6.60 (d, 1H), 3.83 (s, 1H), 1.79 (s, 6H), 0.73 (s, 9H).

e) 2-[2-[3-[3,5-Bis (trifluoromethyl)phenyl]ureido]-4-trifluoromethylphenoxy]-5-(1,1,3,3tetramethylbutyl)benzoic acid 2-(2-amino-4-trifluoromethyphenoxy)-5-(1,1,3,3-tetramethylbutyl)benzoic acid (140 mg, 0.0003 mol) and 3,5-di(trifluoromethyl)phenyl isocyanate (86 μl, 0.0005 mol) were mixed in pyridine (8 ml) at room temperature 16 h. The solvent was evaporated and the residue flash chromatographed (silica gel, ethyl acetate/hexane/formic acid) to yield the title compound; mp 233° C.

EXAMPLE 5

Preparation of 2-[2-[3-[3,5-Bis (trifluoromethyl)phenyl]ureido]-4-trifluoromethyl-phenoxy]-5-(1,1,-dimethylpropyl)benzoic acid a) Methyl-2-hydroxy-5-(1,1-dimethylpropyl)benzoate Following the procedure of Schmitt et al., *Synthesis*, 1984, 758–760; and treating the resulting 2-hydroxy-5-(1,1-dimethylpropyl)benzoic acid with diazomethane gave the title compound. $^1$H NMR (250 MHz, CDCl$_3$) δ10.61 (s, 1H), 7.75 (d, 1H), 7.44 (dd, 1H), 6.92 (d, 1H), 3.95 (s, 3H), 1.61 (q, 2H), 1.26 (s, 6H), 0.67 (t, 3H).

b) Methyl 2-(2-nitro-4-trifluoromethylphenoxy)-5-(1,1-dimethylpropyl)benzoate

Methyl-2-hydroxy-5-(1,1-dimethylpropyl)benzoate (3.0 g, 0.0135 mol), 4-chloro-3-nitrobenzotrifluoride (1.94 ml, 0.013 mol) and potassium carbonate (1.1 g, 0.008 mol) were mixed in dimethylformamide (50 mL) for 3 h. The solvents were evaporated and the residue was flash chromatographed (silica gel, ethyl acetate/hexane) to yield the title compound. $^1$H NMR (250 MHz, CDCl$_3$) δ8.24 (d, 1H); 7.99 (d, 1H), 7.54–7.68 (m, 2H), 7.15 (d, 1H), 6.82 (d, 1H), 3.70 (s, 3H), 1.61–1.76 (m, 2H), 1.32 (s, 6H), 0.65–0.76 (t, 3H).

c) Methyl 2-(2-amino-4-trifluoromethylphenoxy)-5-(1,1-dimethylpropyl)benzoate

Methyl-2-(nitro-4-trifluoromethylphenoxy)-5-(1,1-dimethylpropyl)benzoate (2.5 g, 0.006 mol) was mixed in ethyl acetate (50 mL) and a palladium on carbon catalyst (600 mg) was added under argon. This mixture was hydrogenated at 50 psi for 3 h. The mixture was filtered through Celite ® and washed with methanol and ethyl acetate. The solvents were evaporated to yield the title compound. $^1$H NMR (250 MHz, CDCl$_3$) δ7.84 (d, 1H), 7.44 (dd, 1H), 7.03 (d, 1H), 684–6.97 (m, 2H), 6.72 (d, 1H), 4.22 (s, 2H), 3.81 (s, 3H), 1.55–1.72 (m, 2H), 1.29 (s, 6H), 0.60–0.77 (t, 3H), d) 2-(2-amino-4-trifluoromethylphenoxy)-5-(1,1-dimethylpropyl)benzoic acid Methyl-2(amino-4-trifluoromethyl)phenoxy-5-(1,1-dimethylpropyl)benzoate (650 mg, 0.0017 mol) was saponified in methanol and 1N sodium hydroxide and acidified with 3N hydrochloric acid and water. The aqueous phase was extracted with ethyl acetate. The organic phase was dried (MgSO$_4$) and the solvent evaporated to yield the title compound. $^1$H NMR (250 MHz, CD$_3$OD) δ7.90 (d, 1H), 7.49 (dd, 1H), 7.10 (d, 1H), 6.82–6.96 (m, 2H), 6.75 (d, 1H), 2.05 (s, 1H), 1.68–1.78 (dd, 2H), 1.32 (s, 6H), 0.72 (t, 3H).

e) Benzhydrol 2-(2-amino-4-trifluoromethylphenoxy)-5-(1,1-dimethylpropyl)benzoate 2-(amino-4-trifluoromethylphenoxy)-5-(1,1-dimethylpropyl)benzoic acid (150 mg, 0.0004 mol) was dissolved in toluene and diphenyldiazomethane was added. The mixture was heated to 50° C., under argon, and stirred for 4 h. The solvents were evaporated and the residue was flash chromatographed (silica gel, ethyl acetate/hexane) to yield the title compound. $^1$H NMR (250 MHz, CDCl$_3$) δ7.98 (d, 1H), 7.45 (dd, 1H), 7.24 (s, 10H), 6.83–6.98 (m, 4H), 6.65 (d, 1H), 3.93 (s, 2H), 1.64 (s, 2H), 1.29 (s, 6H), 0.69 (t, 3H).

f) Benzhydrol 2-[2-[3-[3,5-bis (trifluoromethyl)phenyl]ureido]-4-trifluoromethylphenoxy]-5-(1,1-dimethylpropyl)benzoate Benzhydrol-2-(2-amino-4-trifluoromethylphenoxy)-5-(1,1-dimethylpropyl)benzoate (200 mg, 0.0004 mol) and 3,5-di(trifluoromethyl)phenyl isocyanate (300 μL 0.002 mol) were mixed in pyridine, under argon, at room temperature for 16 h. The solvent was evaporated and the residue flash chromatographed (silica gel, ethyl acetate/hexane) to yield the title compound. $^1$H NMR (250 MHz, CDCl$_3$) δ8.69 (d, 2H), 7.97 (d, 1H), 7.59 (s, 2H), 7.48 (d, 2H), 7.20–7.39 (m, 9H), 7.08 (d, 1H), 6.95 (s, 1H), 6.82 (dd, 2H), 2.05 (d, 1H), 1.64 (dd, 2H), 1.32 (s, 6H), 0.99 (d, 1H), 0.72 (t, 3H).

g) 2-[2-[3-[3,5-Bis (trifluoromethyl)phenyl]ureido]-4-trifluoromethylphenoxy]-5-(1,1-dimethylpropyl)benzoic acid Benzhydrol-2-[2-[3-[3,5-bis(trifluoromethyl)phenyl]ureido]-4-trifluoromethylphenoxy]-5-(1,1-dimethylpropyl)benzoate (110 mg, 0.0002 mol) was dissolved in ethyl acetate and a palladium on carbon catalyst (50 mg) was added, under argon. The mixture was hydrogenated in a parr bottle at 54 psi, for 16 h. The mixture was filtered through Celite ® and washed with ethyl acetate and methanol. The solvents were evaporated and the residue was flash chromatographed (silica gel, ethyl acetate/hexane/formic acid) to yield the tide compound; mp 238°–240° C.

Alternative preparation of 2-[2-[3-[3,5-Bis (trifluoromethyl)phenyl]ureido]-4-trifluoromethylphenoxy]-5-(1,1-dimethylpropyl)benzoic acid a) Methyl 2-(2-nitro-4-trifluoromethylphenoxy)-5-(1,1-dimethylpropyl)benzoate Methyl-2-hydroxy-5-(1,1-dimethylpropyl)benzoate (3.0 g, 0.0135 mol), 4-chloro-3-nitrobenzotrifluoride (1.94 ml, 0.013 mol) and potassium carbonate (1.1 g, 0.008 mol) were mixed in dimethylformamide (50 mL) for 3 h. The solvents were evaporated and the residue was flash chromatographed (silica gel, ethyl acetate/hexane) to yield the title compound. $^1$H NMR (250 MHz, CDCl$_3$) δ8.24 (d, 1H), 7.99 (d, 1H), 7.54–7.68 (m, 2H), 7.15 (d, 1H), 6.82 (d, 1H), 3.70 (s, 3H), 1.61–1.76 (m, 2H), 1.32 (s, 6H), 0.65–0.76 (t, 3H).

b) Methyl 2-(2-amino-4-trifluoromethylphenoxy)-5-(1,1-dimethylpropyl)benzoate

Methyl-2-(nitro-4-trifluoromethylphenoxy)-5-(1,1-dimethylpropyl)benzoate (2.5 g, 0.006 mol) was mixed in ethyl acetate (50 mL) and a palladium on carbon catalyst (600 mg) was added under argon. This mixture was hydrogenated at 50 psi for 3 h. The mixture was filtered through Celite ® and washed with methanol and ethyl acetate. The solvents were evaporated to yield the title compound. $^1$H NMR (250 MHz, CDCl$_3$) δ7.84 (d, 1H), 7.44 (dd, 1H), 7.03 (d, 1H), 684–6.97 (m, 2H), 6.72 (d, 1H), 4.22 (s, 2H), 3.81 (s, 3H), 1.55–1.72 (m, 2H), 1.29 (s, 6H), 0.60–0.77 (t, 3H).

c) 2-(2-amino-4-trifluoromethylphenoxy)-5-(1,1-dimethylpropyl)benzoic acid

Methyl-2(amino-4-trifluoromethyl)phenoxy-5-(1,1-dimethylpropyl)benzoate (650 mg, 0.0017 mol) was saponified in methanol and 1N sodium hydroxide and acidified with 3N hydrochloric acid and water. The aqueous phase was extracted with ethyl acetate. The organic phase was dried (MgSO$_4$) and the solvent evaporated to yield the title compound. $^1$H NMR (250 MHz, CD$_3$OD) δ7.90 (d, 1H), 7.49 (dd, 1H), 7.10 (d, 1H), 6.82–6.96 (m, 2H), 6.75 (d, 1H), 2.05 (s, 1H), 1.68–1.78 (dd, 2H), 1.32 (s, 6H), 0.72 (t, 3H).

d) Benzhydrol 2-(2-amino-4-trifluoromethylphenoxy)-5-(1,1-dimethylpropyl)benzoate 2-(amino-4-trifluoromethylphenoxy)-5-(1,1-dimethylpropyl)benzoic acid (150 mg, 0.0004 mol) was dissolved in toluene and diphenyldiazomethane was added. The mixture was heated to 50° C., under argon, and stirred for 4 h. The solvents were evaporated and the residue was flash chromatographed (silica gel, ethyl acetate/hexane) to yield the title compound. $^1$H NMR (250 MHz, CDCl$_3$) δ7.98 (d, 1H), 7.45 (dd, 1H), 7.24 (s, 10H), 6.983–6.98 (m, 4H), 6.65 (d, 1H), 3.93 (s, 2H), 1.64 (s, 2H), 1.29 (s, 6H), 0.69 (t, 3H).

e) Benzhydrol 2-[2-[3-[3,5-bis (trifluoromethyl)phenyl]ureido]-4-trifluoromethylphenoxy]-5-(1,1-dimethylpropyl)benzoate Benzhydrol-2-(2-amino-4-trifluoromethylphenoxy)-5-(1,1-dimethylpropyl)benzoate (200 mg, 0.0004 mol) and 3,5-di(trifluoromethyl)phenyl isocyanate (300 μL 0.002 mol) were mixed in pyridine, under argon, at room temperature for 16 h. The solvent was evaporated and the residue flash chromatographed (silica gel, ethyl acetate/hexane) to yield the title compound. $^1$H NMR (250 MHz, CDCl$_3$) δ8.69 (d, 2H), 7.97 (d, 1H), 7.59 (s, 2H), 7.48 (d, 2H), 7.20–7.39 (m, 9H), 7.08 (d, 1H), 6.95 (s, 1H), 6.82 (dd, 2H), 2.05 (d, 1H), 1.64 (dd, 2H), 1.32 (s, 6H), 0.99 (d, 1H ), 0.72 (t, 3H).

f) 2-[2-[3-[3,5-Bis (trifluoromethyl)phenyl]ureido]-4-trifluoromethylphenoxy]-5-(1,1-dimethylpropyl)benzoic acid Benzhydrol-2-[2-[3-[3,5-bis(trifluoromethyl)phenyl]ureido]-4trifluoromethylphenoxy]-5-(1,1-dimethylpropyl)benzoate (110 mg, 0.0002 mol) was dissolved in ethyl acetate and a palladium on carbon catalyst (50 mg) was added, under argon. The mixture was hydrogenated in a parr bottle at 54 psi, for 16 h. The mixture was filtered through Celite ® and washed with ethyl acetate and methanol. The solvents were evaporated and the residue was flash chromatographed (silica gel, ethyl acetate/hexane/formic acid) to yield the title compound; mp 238°–240° C.

EXAMPLE 6

Preparation of 2-[2-[3-[3,5-Bis (trifluoromethyl)phenyl]ureido]-4-trifluoromethylphenoxy]-4-methoxybenzoic acid a) Methyl 2-(2-nitro-4-trifluoromethylphenoxy)-4-methoxybenzoate Methyl-4-methoxysalicylate (12.0 g, 0.066 mol), 4-chloro-3-nitrobenzotrifluoride (9.75 mL, 0.066 mol) and potassium carbonate (18.16 g, 0.131 mol) were mixed in dimethylformamide, under argon, at 150° C. for 16 h. The reaction mixture was filtered and the solvents evaporated. The residue was flash chromatographed (silica gel, ethyl acetate/hexane) to yield the title compound. $^1$H NMR (250 MHz, CDCl$_3$) δ8.25 (d, 1H), 8.04 (d, 1H), 7.65 (dd, 1H), 6.91 (dd, 1H), 6.81 (d, 1H), 6.70 (d, 1H), 3.88 (s, 3H), 3.70 (s, 3H).

b) Methyl 2-(2-amino-4-trifluoromethylphenoxy)-4-methoxybenzoate

Methyl-2-(nitro-4-trifluoromethylphenoxy)-4-methoxybenzoate (21.65 g 0.058 mol) was dissolved in ethyl acetate and a palladium on carbon catalyst was added under argon. The mixture was hydrogenated in a parr bottle, at 50 psi, for 4 h The mixture was filtered through Celite® and washed with ethyl acetate and methanol. The solvent was evaporated and the residue flash chromatographed (silica gel, ethyl acetate/hexane) to yield the title compound. $^1$H NMR (250 MHz, CDCl$_3$) δ7.92 (d, 1H), 7.03 (d, 1H) 6.90 (dd, 1H) 6.68-6.81 (m, 2H) 6.50 (d, 1H) 4.22 (s, 2H) 3.75 (s, 6H).

c) 2-(2-amino-4-trifluoromethylphenoxy)-4-methoxybenzoic acid

Methyl-2-(2-amino-4-trifluoromethylphenoxy)-4-methoxybenzoate (13.0 g, 0.038 mol) was mixed in tetrahydrofuran and saponified with 1N sodium hydroxide. The solvent was evaporated and the residue mixed in water and acidified with 3N hydrochloric acid, bringing the pH to 4.0. The aqueous phase was extracted with ethyl acetate. The organic phase was dried (MgSO$_4$) and evaporated. The residue was flash chromatographed (silica gel, ethyl acetate/hexane/formic acid) to yield the title compound. $^1$H NMR (250 MHz, methanol d) δ8.00 (d, 1H), 7.10 (d, 1H), 6.88 (dd, 1H), 6.73-6.81 (m, 2H), 6.45 (d, 1H), 3.79 (s, 3H).

d) Benzhydrol 2-(2-amino-4-trifluoromethylphenoxy)-4-methoxybenzoate 2-(2-Amino-4-trifluoromethylphenoxy)-4-methoxybenzoic acid (4.0 g, 0.012 mol) was dissolved in ethyl acetate. Diphenyldiazomethane was dissolved in toluene and added dropwise to the ethyl acetate mixture for 16 h, under argon, in a 50° C. oil bath. The solvent was evaporated and the residue flash chromatographed (silica gel, ethyl acetate/hexane) to yield the title compound. $^1$H NMR (250 MHz, CDCl$_3$) δ8.05 (d, 1H), 7.25 (s, 1H), 7.06 (s, 1H), 6.98 (s, 1H), 6.90 (d, 1H), 6.80-6.70 (m, 2H), 6.52 (d, 1H), 4.01 (s, 2H), 3.80 (s, 3H).

e) Benzhydrol 2-[2-[3-[3,5-bis (trifluoromethyl)phenyl]ureido ]-4-trifluoromethylphenoxy]-4-methoxybenzoate Benzhydrol-2-(2-amino-4-trifluoromethylphenoxy)-4-methoxybenzoate (460 mg, 0.0009 mol) and 3-5-di(trifluoromethyl)phenyl isocyanate (157 μL, 0.0009 mol) were dissolved in pyridine and mixed, under argon, at room temperature for 16 h. The solvent was evaporated and the residue flash chromatographed (silica gel, ethyl acetate/hexane) to yield the title compound. $^1$H NMR (250MHz, CDCl3) δ8.75 (s, 1H), 8.61 (d, 1H), 8.00 (q, 2H), 7.42-7.52 (m, 1H), 7.12-7.32 (s, 10 H), 7.00 (d, 1H), 6.65-6.90 (m, 2H), 6.50 (d, 1H), 6.42 (d, 1H), 3.76 (s, 3H), 4.00 (s, 2H).

f) 2-[2-[3-[3,5-Bis (trifluoromethyl)phenyl]ureido]-4-trifluoromethylphenoxy]-4methoxybenzoic acid Following the procedure of Example 23(g), except substituting benzhydrol-2-[2-[3-[3,5-bis(trifluoromethylphenyl]ureido-4-trifluoromethylphenoxy]-4-methoxybenzoate, the title compound was prepared; mp 248° C.

EXAMPLE 7

Preparation of 2-[2-[3-[3,5-Bis(trifluoromethyl)phenyl]ureido]-4-trifluoromethylphenoxy]benzoic acid a) 2-[2-[3-[3,5-Bis(trifluoromethyl)phenyl]ureido]-4-trifluoromethylphenoxy]benzoic acid 2-(2-Amino-4-trifluoromethylphenoxy)benzoic acid (0.17 g, 0.57 mmol) was dissolved in pyridine (2 mL) and stirred under argon at room temperature. Bis 3,5-(trifluoromethyl)phenyl isocyanate (0.167 mL, 1 mmol) was added and the mixture stirred for 16 h. The solvent was evaporated and the residue was flash chromatographed (silica gel, ethyl acetate/hexane/formic acid) and then recrystallized from ethyl acetate/hexane to give the title compound as a white crystalline solid; mp 229°-231° C.

EXAMPLE 8

Preparation of Methyl 2-[2-[3-[3,5-Bis(trifluoromethyl)phenyl]ureido]-4-trifluoromethylphenoxy]benzoate a) Methyl 2-[2-[3-[3,5-Bis(trifluoromethyl)phenyl]ureido]-4-trifluoromethylphenoxy]benzoate Following the procedure of Example 7 except substituting methyl 2-(2-amino-4-trifluoromethylphenoxy)benzoate for 2-(2-amino-4-trifluoromethylphenoxy)benzoic acid, and eluting the column with ethyl acetate/hexane instead of ethyl acetate/hexane/formic acid, gave the title compound as a white crystalline solid mp 210°-211° C.

EXAMPLE 9

Preparation of 2-[2-[3-(Octyl)ureido]-4-trifluoromethylphenoxy]benzoic acid a) Methyl 2-(2-nitro-4-trifluoromethylphenoxy)benzoate A mixture of methyl salicylate (7.6 g, 0.05 mol), 4-chloro-3-nitrobenzotrifluoride (7.46 ml, 0.05 mol) and potassium carbonate (4.14 g, 0.03 mol) in dimethylformamide (50 ml) was stirred under argon, in an oil bath at 150° C., for three hours. The reaction mixture was diluted with ethyl acetate and filtered. The filtrate was evaporated and the residue flash chromatographed (silica gel, ethyl acetate/hexane) to give the title compound. $^1$H NMR (250 MHz, CDCl$_3$) δ8.29 (d, 1H), 8.05 (dd, 1H), 7.61 (m, 2H), 7.4 (t, 1H), 7.25 (t, 1H), 6.85 (d, 1H), 3.7 (s, 3H).

b) Methyl 2-(2-amino-4-trifluoromethylphenoxy)benzoate

A mixture of methyl 2-(2-nitro-4-trifluoromethylphenoxy)benzoate (12.7 g, 0.0373 mol) was dissolved in ethyl acetate (200 ml) and 10% palladium on carbon was added under argon. The mixture was hydrogenated in a parr bottle at 55 psi for three hours. The mixture was diluted with chloroform, filtered through Celite® and the filtrate evaporated. The residue was flash chromatographed (silica gel, ethyl acetate/hexane) to give the title compound.

c) 2-(2-amino-4-trifluoromethylphenoxy)benzoic acid

Methyl 2-(2-amino-4-trifluoromethylphenoxy)benzoate (11.68 g, 0.0375 mol) was mixed in tetrahydrofuran (175 ml) and sodium hydroxide (77 ml) at 40° C. for sixteen hours. The solvents were evaporated and water added to the residue. 3N hydrochloric acid was then added to the mixture until the maximum precipitate was given. The aqueous mixture was extracted with ethyl acetate (3×) and the organic phase dried over MgSO4 and evaporated. The residue was flash chromatographed (silica gel, methylene chloride/ethanol/ammonium hydroxide) to give the title compound. $^1$H NMR (250 MHz, CD$_3$OD) δ7.90 (dd, 1H), 7.5 (tt, 1H), 7.2 (tt, 1H), 7.09 (d, 1H), 6.95 (dd, 1H), 6.85 (dd, 1H), 6.75 (d, 1H).

d) Benzhydrol 2-(2-amino-4-trifluoromethylphenoxy)benzoate 2-(2-amino-4-trifluoromethylphenoxy)benzoic acid (2.63 g, 0.00848 mol) was dissolved in ethyl acetate (30 ml) and diphenyldiazomethane (2.26 g, 0.0116 mol) dissolved in toluene (50 ml) was added dropwise. The reaction was stirred for sixteen hours. The solvents were evaporated and the residue was flash chromatographed (silica gel, ethyl acetate/hexane) to give the title compound. $^1$H NMR (250 MHz, CDCl$_3$) δ8.0 (dd, 1H), 7.49 (tt, 1H), 7.2 (m, 10H), 7.0 (d, 1H), 6.95 (dd, 2H), 6.86 (dd, 1H), 6.71 (d, 1H) 3.98 (s, 2H),1.56 (s 1H).

e) Benzhydrol 2-[2-[3-(octyl) ureido]-4-trifluoromethylphenoxy)benzoate

Benzhydrol 2-(2-amino-4-trifluoromethylphenoxy)-benzoate (700 mg, 0.0015 mol) was dissolved in pyridine and octylisocyanate (412 mg, 0.0027 mol) was added to the mixture at room temperature and stirred for three hours. The solvent was evaporated and the residue was flash chromatographed (silica gel, ethyl acetate/hexane) to give the title compound. $^1$H NMR (250 MHz, CDCl$_3$) δ8.7 (s, 1H), 8.2 (s, 1H), 7.95 (d, 1H), 7.29 (m, 10H), 7.12 (s, 1H), 7.1 (d, 1H), 7.0 (s, 1H), 6.9 (d, 1H), 4.8 (s, 1H), 3.1 (dd, 1H), 1.28 (s, 14H), 0.85 (t, 3H).

f) 2-[2-[3-(Octyl)ureido]-4-trifluoromethylphenoxy]benzoic acid

A mixture of benzhydrol 2-[2[3-(octyl)ureido]-4-trifluoromethylphenoxy)-benzoate (290 mg, 0.00047 mol) and 10% palladium on carbon (100 mg) in ethyl acetate was hydrogenated in a parr bottle, at 55 psi for three hours. The mixture was diluted with chloroform, filtered through Celite and the filtrate evaporated. The residue was flash chromatographed (silica gel, ethyl acetate/hexane/formic acid) to give the title compound. $^1$H NMR (250 MHz, CD$_3$OD) δ8.52 (d, 1H), 7.95 (dd, 1H), 7.6 (tt, 1H), 7.35 (tt, 1H), 7.14 (dd, 2H),6.7 (d, 1H), 3.15 (t, 1H), 1.3 (s, 14H) 0.85 (t, 3H).

The following compounds may also be madeby one of skill in the art using methods analagous to the Examples indicated above.

Example 10: 2-[2-(Nonanamido)phenoxy]benzoic acid; m.p. 81°–82° C.

Example 11: 2-[2-[3-(Octyl)ureido]phenoxy]benzoic acid; m.p. 138°–139° C.

Example 12: 2-[2-[3,5-Bis-(trifluoromethyl)]benzamido- 4-trifluoromethylphenoxy]benzoic acid; m.p. 178° C.

Example 13: 2-[2-[3-(4-Chlorophenyl)ureido]phenoxy]benzoic acid; m.p. 195°–196° C.

Example 14: 2-[2-[3-[4-Chloro-3-(trifluoromethyl)-phenyl]ureido]phenoxy]benzoic acid; m.p. 215°–216° C.

METHODS OF TREATMENT

The compounds of Formula (I) or pharmaceutically acceptable salts thereof can be used in the manufacture of a medicament for the prophylactic or therapeutic treatment of an inflammatory disease state in a mammal, preferably a human.

Inhibition of PLA$_2$ and/or CoA-IT and the simultaneous reduction of PAF, free arachidonic acid and eicosanoid release from inflammatory cells according to this invention is of therapeutic benefit in a broad range of diseases or disorders. The invention herein is therefore useful to treat such disease states both in humans and in other mammals.

Inhibition of CoA-IT and 14 kDa PLA$_2$ by the compounds of Formula (I) is an effective means for simultaneously reducing PAF, free arachidonic acid and eicosanoids produced in inflammatory cells. The therapeutic utility of blocking lipid mediator generation has been recognized for many years. For example, inhibitors of cyclooxygenase, such as aspirin, indomethacin, acetaminophen and ibuprofen, have demonstrated broad therapeutic utilities. CoA-IT inhibitors inhibit cyclooxygenase products. Another class of inhibitors which are used in a broad range of inflammatory disorders are the corticosteroids. Corticosteroids act in a variety of ways, e.g. to induce inflammatory cells to produce proteins which inhibit free arachidonic acid release or to down regulate PLA$_2$ mRNA formation. Both 14 kDa PLA$_2$ inhibitors and CoA-IT inhibitors block the release of free arachidonic acid. Inhibitors of 5-lipoxygenase block the production of leukotrienes and leukotriene antagonists prevent the bioactions of leukotrienes. Recent studies indicate that both will have broad therapeutic utilities. Both 14 kDa PLA$_2$ inhibitors and CoA-IT inhibitors block the production of leukotrienes. Inhibitors of phospholipase A$_2$ block the release of free arachidonic acid and the formation of lyso PAF (the immediate precursor of PAF). PLA$_2$ inhibitors are recognized to have broad therapeutic utilities. It does not, however, follow that the disease states noted above must in fact be caused by altered CoA-IT or PLA$_2$ activity. Thus, the disease state itself may not be directly mediated by CoA-IT or PLA$_2$ activity. It only follows that CoA-IT or PLA$_2$ activity is required for the continued expression of symptoms of the disease state and that CoA-IT or PLA$_2$ inhibitors will be beneficial against the symptoms of these disease states.

Recognition that 14 kDa PLA$_2$ and/or CoA-IT inhibitors reduce PAF production has a number of therapeutic implications. PAF itself has been implicated as being involved in a number of medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock.

Intravenous infusion of PAF at doses of 20–200 pmol kg<−1>min<−1>into rats has been reported to result in the formation of extensive haemorrhagic erosions in the gastric mucosa. Thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role is the disease of psoriasis. And finally, increasing evidence supports a potential patho-physiological role for PAF in cardiovascular disease. Thus recent studies in angina patients show PAF is released during atrial pacing. Intracoronary injection of PAF in pigs induces a prolonged decrease in coronary flow and, in guines pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke. Thus the compounds of the invention, by virtue of their ability to antagonise either CoA-IT and/or $PLA_2$, thus block the production of PAF, free arachidonic acid and its metabolites, are likely to be of value in the treatment off any of the above conditions.

The action of a $PLA_2$ inhibitor can be distinguished from the activity of a CoA-IT inhibitor based on their specific actions on their respective enzymes and by their different effects in cellular assays. For example only CoA-IT inhibitors have the ability to interfere with the mobilization of radiolabelled arachidonic acid to move from the alkyl-PC pool to the alkenyl PE pool. Selective inhibitors of 14 kDa $PLA_2$ are without an effect in this assay (assay E). Alternatively, CoA-IT inhibitors will inhibit both LTC4 and PGE2 release from activated monocytes while selective $PLA_2$ inhibitors inhibit LTC4 release but spare prostanoid formation or production (assay F).

Disease states which could benefit from the inhibition of lipid mediator production include, but are not limited to, adult respiratory distress syndrome, asthma, arthritis, reperfusion injury, endotoxic shock, inflammatory bowel disease, allergic rhinitis and various inflammatory skin disorders. Each of these disorders is mediated in some part by lipid mediators of inflammation. Compounds which inhibit CoA-IT, by virtue of their ability to block the generation of lipid mediators of inflammation, are of value in the treatment of any of these conditions. Similarly compounds which inhibit $PLA_2$, by virtue of their ability to block the generation of lipid mediators of inflammation stemming from activation and/or release of this enzyme are of value in the treatment of these conditions. In particular, an inhibitor of CoA-IT, for instance would offer an advantage over the classical NSAIDs which affect only prostanoid production (and not PAF biosynthesis) thereby inhibiting both the acute and cell-mediated "chronic" inflammatory processes. Further an advantage of the $PLA_2$ inhibitor would be their affect on human monocyte leukotrienes and PAF formation, while immunosuppressive prostanoids, such as PGE2, are spared.

Treatment of disease states caused by these lipid inflammatory mediators i.e., arachidonate, eicosanoids and PAF, include certain cardiovascular disorders such as but not limited to, myocardial infarction, stroke, circulatory shock, or hypotension, ischemia, reperfusion injury; inflammatory diseases such as, but not limited to, arthritis, inflammatory bowel disease, Crohn's disease, or ulcerative colitis; respiratory diseases, such as but not limited to, asthma, or adult respiratory distress syndrome; analphylaxis, shock, such as but not limited to endotoxic shock; topical disesases, such as but not limited to actinic keratosis, psoriasis, or contact dermatitis; or pyresis.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. Such pharmaceutically acceptable carriers or diluents and methods of making are well known to those of skill in the art, and reference can be found in such texts as Remington's Pharmaceutical Sciences, 18th Ed., Alfonso R. Genarao, Ed., 1990, Mack Publishing Co. and the Handbook of Pharmaceutical Excipents, APhA Publications, 1986.

The compounds of formula (I) may also be administered in conventional dosages in combination with known second therapeutically active compounds, such as steroids or NSAID's for instance. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical career employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Each dosage unit for oral administration contains preferably from 1 to 250 mg (and for parenteral administration contains preferably from 0.1 to 25 mg) of a compound of the structure (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the Formula (I) or a pharmaceutically acceptable salt thereof calculated as the free base, the compound being administered from 1 to 4 times per day.

The choice of form for administration, as well as effective dosages, will vary depending, inter alia, on the condition being treated. The choice of mode of administration and dosage is within the skill of the art.

BIOLOGICAL METHODS

To determine activity of the compounds of Formula (I) various cellular assays can be used to determine in vitro activity. Additionally, various classical in vivo acute inflammatory models which have some aspect of their etiology to elevated eicosanoid levels can be employed, such as the paw edema model, mouse zymosan peritonitis, reverse Arthus pleurisy or various skin inflammation assays which are described in Lewis et al., Experimental Models of Inflammation, in the *Handbook of Inflammation*, Vol. 5, Bonta Ed., Elsevier Science Publishers, New York (1985) whose disclosure is herein incorporated by reference. The TPA induced ear edema model (mouse) as well as the carrageenan paw edema model in the rat are described herein as well. These classical models of inflammation will reflect the drugs ability to alter an inflammatory response but cannot address the specificity of drug action. These models have been traditionally designed as non steriod antiinflammatory drug sensitive pharmacological screens and it is important to utilize models which can differentiate PLA2 and CoA-IT inhibitors from NSAIDS.

Cell-free and Celllular Assessment of Inhibitors

Described herein are several in vitro assays both for CoA-IT and $PLA_2$ enzyme activities. The first employes purified recombinant enzyme or a broken cell assay, assay (a or b, respectively) described below. Alternatively, evaluation of inhibitors can occur in intact cells such as described in the assay, assay (c and d) below. CoA-IT activity can exclusively be measured, and differentiated from $PLA_2$ inhibition, in intact cells by following the movement of a pulse of [$^3$H] arachidonate as it moves into the 1-alkyl and 1-alkenyl phospholipids in inflammatory cells (assay e). It should be noted for the purposes herein that assays c, d, & f can both be used for $PLA_2$ and CoA-IT inhibition determination.

Inflammatory Responses in vivo

The ability of compounds that inhibit CoA-IT and/or $PLA_2$ to affect in vivo inflammatory responses may be assessed. Inflammatory responses are induced in the mouse ear by the topical application of a pro-inflammatory agent, such as 12-0-tetradecanoylphorbol 13-acetate (assay g). This produces an edematous response, as measured by increases in ear thickness, as well as increased inflammatory cellular infiltrate, as measured by increases in myeloperoxidase activity (as described in the methods). To further validate the mechanism of action inflammation induced by the direct adminstration of arachidonic acid can be used. In this case compounds altering arachidonic acid mobilization or liberation should be with our effect.

In Vitro Assays

Assay (a): Phospholipase $A_2$ assay:

Phospholipase $A_2$ activity of rh Type II- 14 kDa $PLA_2$ or $PLA_2$ semi-purified from human synovial joint fluid was measured by the acylhydrolysis of high specific activity (NEN)[$^3$H]-AA-*E. coli* (0.5 mCi/5 nmol PL Pi) as previously described in Marshall et al., J. Rheumatology, 18:1, pp59–65 (1991). High specific activity [$^3$H]AA-*E. coli* had up to 95% of the label incorporated into phospholipid which was localized almost exclusively in the sn-2 position, as demonstrated by purified 14kDa $PLA_2$ or low molecular weight $PLA_2$ acylhydrolysis and separation of products by thin layer chromatography (TLC) (data not shown). [Predominately used herein was rh Type II 14 kDa $PLA_2$, or alternatively bovine pancreatic $PLA_2$ was also be used]. The reaction mixture (50 or 100 ml total volume) contained 25 mM HEPES, pH 7.4, 150 mM NaCl, 5 mM $CaCl_2$ and [$^3$H]-AA-*E. coli* (low specific activity; 5–8 nmol PL Pi per assay). Assays were incubated for a time predetermined to be on the linear portion of a time versus hydrolysis plot. Experiments were conducted with final % hydrolysis values ranging from 2% (400–1000 dpm) to 10% (2000–5000 dpm) acylhydrolysis after blank correction. Reactions were terminated by the addition of 1.0 mL tetrahydrofuran (THF). The whole sample was placed over aminopropyl solid phase silica columns and eluted with THF:acetic acid (49:1) exclusively separating free fatty acids with greater than 95% recovery. Radiolabel in this eluate was quantitated by liquid scintillation counting. Results were expressed as % of fatty acid hydrolyzed ([sample dpms—nonspecific (blank) dpms/total dpms]×100) or specific activity which was calculated from hydrolysis values found in the linear portion of time versus % hydrolysis plots (pmol free fatty acid hydrolyzed/mg/min). Non-specific activity was always less than 1% of the total counts added.

Protein determination

All protein concentrations were determined by Bradford protein analysis kits (Biorad, Richmond, Calif.).

Results

Representative compounds of Formula (I), Examples 1 to 14 all demonstrated positive $PLA_2$ inhibition in the method noted above. While these compounds generally tested positive at 50 μm levels, several were also tested for positive inhibitory activity at up to 500 μM levels.

Assay (b): CoA-IT Activity

The following is a method to measure CoA-IT activity and the effects of compounds on CoA-IT activity. The assay is based upon mixing cellular material containing CoA-IT activity with a stable lyso phospholipid such as 1-alkyl-2-acyl-GPC and measuring the production of phospholipid product such as 1-alkyl-2-acyl-GPC occurring in the absence of added CoA or CoA-fatty acids.

Cell Preparation

Any inflammatory cell that contains high levels of CoA-IT activity can be used, such as neutrophils, macrophages or cell lines such as U937 cells. U937 cells were obtained from American Type Culture Collection and grown in RPMI-1640 media (Gibco, Grand Island, N.Y.) supplemented with 10% fetal bovine serum (Hyclone, Logan, UT) at 37° C., 5% $CO_2$. Cells were grown without differentiation (basal state) by any agent, such as dimethyl sulfoxide. As used herein, "inflammatory cells" include, but are not limited to neutrophils, macrophages, monocytes, lymphocytes, eosinophils, basophils, and mast cells.

Microsomal preparation

Microsomes were prepared using standard techniques. In this case, cells were washed with a buffer of 250 mM sucrose, 10 mM Tris, 1 mM EGTA, 1 mM $MgCl_2$, pH 7.4 and ruptured by $N_2$ cavitation (750 psi, 10 minutes). The ruptured cells were centrifuged 1000× g, 5 minutes. The resulting supernatant was centrifuged at 20,000×g,~20 minutes. Microsomes were prepared from this supernatant by centrifugation at 100,000× g, 60 minutes. The resulting pellet was washed once with assay buffer (150 mM NaCl, 10 mM $Na_2KPO_4$, 1 mM EGTA, pH 7.4), recentrifuged and the pellet resuspended in assay buffer (4–20 mg protein/ml) and was stored at −80° C. until assayed.

CoA-IT activity

CoA-IT activity was measured in 1.5 ml centrifuge tubes in a total volume of 100 ul. Microsomes were diluted in assay buffer to the desired protein concentration (6–20 ug/tube). The reaction was initiated by addition of [3H] 1-alkyl-2-lyso-sn-glycero-3-phosphocholine (GPC)(~0.1 uCi/tube) and 1 μM final cold 1-alkyl-2-lyso-GPC in assay buffer with 0.25 mg/ml fatty acid-poor bovine serumalbumin (BSA) (Calbiochem, La Jolla, Calif.). [3H]1-alkyl-2-lyso-GPC, approximately 50 Ci/mmol, was from NEN-Dupont (Boston, Mass.) and cold 1-alkyl-2-lyso-GPC was from Biomol (Plymouth Meeting, Penn.). Microsomes were pretreated with desired agents for the desired time (10 minutes) before the addition of [3H]1-alkyl-2-lyso-GPC. The reaction was run for the desired time (10 minutes) at 37° C. The reaction was stopped and the lipids extracted by addition of 100 ul of chloroform:methanol (1:2, v/v) followed by 100 ul of chloroform and 100 ul of 1M KCl. The samples were vortexed and centrifuged at high speed in a microfuge for 2–3 minutes. An aliquot of the chloroform-extracted materials were separated, usually by TLC in chloroform/methanol/acetic acid/water (50:25:8:4, v/v), visualized by radioscanning (Bioscan) and the product, [3H] 1-alkyl-2-acyl-GPC, was scraped and quantified by liquid scintillation spectroscopy. With this TLC system, the synthetic standards of 1-alkyl-2-lyso-GPC and 1-alkyl-2-acyl-GPC were well separated, with Rf values of approximately 0.25 and 0.65, respectively. Other methods can be used to separate substrate from product, including but not limited to column chromatography, affinity chromatography and post reaction derivitization.

Protein concentration were assessed using the protein assay reagents from Bio-Rad (Richmond, Calif.).

Results

A variety of compounds have been tested in this assay to determine its selectivity and inability to detect trivial, non-selective inhibitors. Inhibitors of 5-lipoxygenase (5-LO) and cyclooxygenase (CO), such as indomethicin, naproxen, 6-(4'-Fluorophenyl)-5-(4-pyridyl)-2,3-dihydroimidzo-[2,1-b]thiazole and 6-(4'-Fluorophenyl)-5-(4-pyridyl)2,3-dihydroimidzo-[2,1-b]thiazole-dioxide had no effect on CoA-IT activity at concentrations up to 100 μM. The anti-oxidant BHT also has no effect at concentrations up to 100 μM. Compounds which complex with phospholipids and inhibit $PLA_2$ activity, such as quinacrine and aristolochic acid have no effect on CoA-IT activity at concentrations up to 500 μM. Doxepine, a compound reported to inhibit PAF release did not inhibit CoA-IT at concentrations up to 100 μM. Sodium diclofenac, reported to decrease leukotriene production by altering arachidonic acid metabolism, had no effect on CoA-IT activity at concentrations up to 500 μM. These results show that the assay for CoA-IT activity is sensitive and selective.

Representative compounds of Formula (I) which inhibit CoA-IT activity in the microsomal CoA-IT assay (assay (a) above) [generally at 50 μM or less] are the compounds:

2-[2-[3-[3,5-Bis(trifluoromethyl)phenyl]ureido]phenoxy]benzoic acid

2-[2-[3-(4-Bromophenyl)ureido]-4-trifluoromethylphenoxy]benzoic acid;

2-[2-[3-[3,5-Bis(trifluoromethyl)phenyl]ureido]-4-(trifluoromethyl)-phenoxy]-5-(1,1,3,3-tetramethylbutyl)benzoic acid 2-[2-[3-[3,5-bis(trifluoromethyl)phenyl]ureido]-4-trifluoromethyl-phenoxy]5-( 1,1-dimethylpropyl)benzoic acid 2-[2-[3-[3,5-Bis(trifluoromethyl)phenyl]ureido]-4-trifluoro-methylphenoxy]benzoic acid Methyl 2-[2-[3-[3,5-bis(Trifluoromethyl)phenyl]ureido]-4-trifluoromethylphenoxy]benzoate; and 2-[2-[3-(Octyl)ureido]-4-trifluoromethylphenoxy]benzoic acid Assay (c): Arachidonic Acid Release Assay
Preparation of human neutrophils Human neutrophils are obtained in the laboratory using three different methods. One method uses leukophoresis packs from normal humans and neutrophils are isolated using the histopaque-1077 technique. The blood is centrifuged at 300× g for 10 minutes. The cell pellets am resuspended in PBS composed of 137 mM NaCl, 8.8 mM Na2HPO4, 1.5 mM KH2PO4, 2.7 mM KCI (Dulbecco's Gibco Laboratories, Long Island, N.Y.) and layered over histopaque-1077 (Sigma, St. Louis, Mo.). The pellets are collected after centrifugation (300× g for 30 minutes) and washed once in PBS. The cell pellets are exposed briefly to deionized water to lyse any erythrocytes. The remaining cells are collected by centrifugation, suspended in PBS, counted and identified after cytospinning and staining. The final leukocyte preparation will be of greater than 95% purity and viability.

The second method isolates human neutrophils from fresh heparinized normal blood using the Histopaque-1077 technique. The blood is layered over Histopaque-1077 (Sigma, St. Louis Mo.) and centrifuged at 400× g for 30 minutes. The cell pellets are resuspended in 35 ml of PBS and 12 ml of 6% Dextran, followed by Dextran sedimentation at room temperature for 45 minutes. The upper layer is collected and further centrifugated for 10 minutes at 1000 rpm. The cell pellets are exposed briefly to deionized water to lyse erythrocytes. The remaining cells are collected by centrifugation, suspended in PBS, counted and identified after cytospinning and staining. The final leukocyte preparation will be of greater than 95% purity and viability.

The third method isolates human neutrophils from freshly drawn heparinized normal blood using the Percoll technique. The blood is first treated with 6% Dextran at room temperature for a 1 hour sedmination. The upper layers of plasma are collected and centrifuged at 400× g for 10 minutes. The cell pellets are resuspended in Percoll 1.070 g/ml supplemented with 5% fetal bovine serumand layered on discontinuous gradients (1.080, 1.085, 1.090,1.095 g/ml) followed by centrifugation at 400× g for 45 minutes. The neutrophils are collected from interfaces of 1.080 and 1.085 and the 1.085 and 1.090 Percoll densities, followed by a centrifugation at 400× g for 45 minutes. The neutrophils are suspended in PBS, counted and identified after cytospinning and staining. The final leukocyte preparation will be of greater than 95% purity and viability.

There should be no difference noted in the response of the neutrophils nor in the effects of test compounds in neutrophils isolated by the three different techniques.

Treatment of human neutrophils

Neutrophils are suspended in PBS with 1 mM $Ca^{2+}$ and 1.1 mM $Mg^{2+}$ at concentrations of 5 to $20\times10^6$ cells per ml. Cells are added to test tubes and treated with the desired compounds for 5 to 10 minutes, then challenged with calcium ionophere A23187, 2 μM, or vehicle control, PBS containing 0.25–1 mg/ml BSA. After 5 to 20 minutes, the reactions are terminated by addition of an equal volume of chloroform:methanol (1:2, v/v) to the samples. [$^2H_8$]Arachidonic acid (50, 100 or 200 ng) is added as an internal standard and the lipids ware extracted by addition of equal volumes of chloroform and distilled water. The samples are vortexed and centrifuged at high speed and the chloroform layer removed to a clean tube.

Assay for free arachidonic acid

The chloroform extract for each sample was evaporated to dryness and the material resuspended in hexane. The hexane was passed through a Silica solid phase column (500 mg), washed 2× with hexane and a fatty acid enriched fraction eluted with hexane:ethyl ether (1:1, v/v). Solvents were removed from the samples under a stream of nitrogen then the samples were converted to pentafluorobenzyl esters using pentafluorobenzyl bromide and diisopropylethylamine in acetonitrile. Solvents were removed and samples were suspended in hexane. GC/MS analysis is performed on a suitable instrument, such as a Finnigan MAT TSQ 700 GC/MS/MS/DS (San Jose, Calif.) operated as a single stage quadruple system or a Hewlett-Packard 5890 with a 5989A M5 system.

The peaks corresponding to arachidonic acid and [$^2H_8$]Arachidonic acid were identified and the areas of those peaks compared and the released arachidonic acid calculated as ng of arachidonic acid for each sample.

Protein concentrations are assessed using the protein assay reagents from Bio-Rad (Richmond, Calif.).

Assay (d): Assay for Production of Platelet-Activating Factor (PAF)

Preparation of human neutrophils

Blood is obtained from normal humans and neutrophils were isolated as described for the arachidonic acid release assay, above. The final leukocyte preparation should be of greater than 95% purity and viability.

Treatment of human neutrophils

Neutrophils were suspended in PBS at concentrations of 5 to $20\times10^6$ cells per ml. Cells were added to test tubes and treated with the desired compounds for 5 to 10 minutes, then challenged with calcium ionophore A23187, 2 μM and 20–30 μCi of [3H]acetic acid (NEN-Dupont, Boston, Mass.), or the vehicle of PBS with 0.25–1 mg/ml. After 5 to 20 minutes, the reactions were terminated by addition of an equal volume of chloroform:methanol (1:2, v/v) to the samples and the lipids were extracted by addition of equal volumes of chloroform and distilled water. The samples were vortexed and centrifuged at high speed and the chloroform layer removed to a clean tube.

Assay for PAF

The chloroform from each tube was evaporated to dryness and the material suspended in a small volume of chloroform or chloroform:methanol (25–100 μl) and the total material spotted on a Silica TLC plate. The plates were developed in chloroform/methanol/acetic acid/water (50:25:8:4, v/v) visualized by radioscanning (Bioscan) and the product, [3H]PAF, was scraped and quantified by liquid scintillation spectroscopy. With this TLC system, the Rf value for a synthetic standard of PAF is approximately 0.33.

Representative compounds of Formula (I) herein which demonstrated positive activity, i.e., inhibition of PAF production, in this assay are:

2-[2-[3-[3,5-Bis(trifluoromethyl)phenyl]ureido]-4-trifluoro-methylphenoxy]benzoic acid; and 2-[2-[3-[3,5-Bis(trifluoromethyl)phenyl]ureido]phenoxy]benzoic acid.

Assay (e): Methods for the evaluation Of COA-IT inhibitors on mobilization of labeled arachidonic acid in intact cells Measurement of the effect of CoA-IT inhibitors on the transfer of [$^3$H]arachidonate into 1-ether phospholipids in non-stimulated inflammatory cells can be accomplished by general application of the following specific method. Human neutrophils were isolated and resuspended ($5 \times 10^7$/ml) in Hanks Balanced Salt Solution (HBSS; Gibco). [5,6,8,9,11,12,14,15-$^3$H]-Arachidonic acid (100 Ci/mmol; New England Nuclear) complexed to 200 μl HBSS containing 0.25 mg/ml HSA was added to the cell suspension (1 μCi/ml). The cells were incubated with gentle shaking at 37° C. for 5 min. The reaction was terminated by the addition of 40 ml ice-cold HBSS containing HSA (0.25 mg/ml). The cells were then removed from the supernatant fluid by centrifugation (225 g, 8 min). Unincorporated [$^3$H]-arachidonic acid was completely removed by two more washes of HBSS containing 0.25 mg/ml HSA. The neutrophils were resuspended in fresh buffer, exposed to various concentrations of a CoA-IT inhibitor or its vehicle and incubated without stimulation for 2 hrs. At that time, the tubes containing the cells and buffer were extracted (Bligh & Dyer [Can. J. Biochem. Physiol. (1959) 37,911–917]) and the phospholipid classes separated and collected by normal phase HPLC, using a Ultrasphere Silica column (4.6 mm×250 mm; Rainin) eluted with hexane/2-propanol/ethanol/phosphate buffer (pH 7.4)/acetic acid (490:367:100:30:0.6 v/v) for 5 min at a flow rate of 1 ml/min. The amount of phosphate buffer in the eluting solvent was increased to 5 % over 10 min and this solvent composition was maintained until all the phospholipid classes had eluted from the column (30–40 min) (Chilton, F. H. [Methods Enzymol. (1990)187, 157–166]). The phospholipids were converted into diradylglycerols by addition of phospholipase C, 20 units–40 units of *Bacillus cereus* phospholipase C (Sigma Type XIII) in 100 mM Tris HCl buffer (pH 7.4) for 2.5–6 hr, then converted into 1,2- diradyl-3-acetylglycerols by incubation with acetic anhydride and pyridine (Chilton, F. H. [Methods Enzymol. (1990)187, 157–166]). The phospholipid subclasses were separated by TLC in benzene/hexane/ethyl ether (50:45:4, v/v), located by image analysis (Bioscan) and the amount of radioactivity in each class was determined by zonal scraping and liquid scintillation counting.

The following is the method for assessing the ability of a compound to alter arachidonate content of cellular phospholipids, which can be generalized for any desired cell. Specifically, mouse bone marrow-derived mast cells are removed from culture and provided with exogenous [$^3$H]arachidonic acid for 30 minutes. The labeled arachidonic acid which had not been incorporated into the cells is then removed by washing the cells 2 times with an albumin-containing buffer. At that point, the cells are treated with various concentrations of CoA-IT inhibitors and then placed back in culture for 24–48 hours. The phospholipids are extracted by the method of Bligh and Dyer [Can. J. Biochem. Physiol. (1959) 37, 911–917]and phospholipids separated by normal phase HPLC by the method of Chilton [Methods Enzymol. (1990)187, 157–166]. The radioactive and mole quantities of arachidonate in complex lipids are determined. At this point, cellular lipid extracts are treated with KOH (0.5M) to remove fatty acids from complex lipids (phospholipids) and the quantities of arachidonate in these extracts can then be determined by various methods, including gas chromatography and mass spectrometry (Chilton [Methods Enzymol. (1990)187, 157–166]).

Assay (f): Measurement of stimulated eicosanoid release by human monocytes.

Human Monocyte Isolation

Leukocyte-rich leukopaks obtained from Biological Specialties (Lansdale, Pa.) were collected from male volunteers who were not taking anti-inflammatory drugs. Leukopaks were centrifuged ($90 \times$ g for 15 min) twice to remove the platelet-rich plasma. The cell pellet was washed by centrifugation and resuspended in HBSS without $Ca^{2+}$ or $Mg^{2+}$. Histopaque 1077 was layered under the cell suspension and centrifuged at $400 \times$ g for 30 min to obtain the buffy coat. The interfacial buffy coat, containing monocytes and lymphocytes, was removed and saved. The buffy coat was washed twice with HBSS without $Ca^{2+}$ or $Mg^{2+}$ by centrifugation. The cell pellet ($4-6 \times 10^8$ cells/30 mls) was resuspended in iso-osmotic media (RPMI-1640, 10% heat inactivated fetal bovine serum (FBS), 0.2 mM L-glutamine, 2.5 mM HEPES) and layered over an equal volume of 46% Percol mixture (10X PBS/Percol; 9.25/0.75) and 54% iso-osmotic media and centrifuged for 30 min at $1000 \times$ g (Marshall and Roshak, Biochem. Cell Biol. 71: 331–339, 1993). The monocyte population located at the interface of the Percoll gradient was removed and washed twice in HBSS without $Ca^{2+}$ or $Mg^{2+}$. This resulted in a greater than 85–90% pure monocyte population as assessed by differential staining.

Measurement of Stimuli-Induced Eicosanoid Release

Monocytes ($5 \times 10^6$/ml) were incubated as a suspension in serum-free RPMI- 1640 medium containing the vehicle DMSO (<1%) or drug for 30 min at 27° C. after which vehicle or stimuli was added for the indicated time. The stimulating agent is solubilized in DMSO and appropriate vehicle controls were included in all experiments. The amount of stimuli was chosen from the linear portion of a concentration versus product curve usually representing 60–80% maximal stimulation over the indicated incubation time at 37° C. (A23187, 1 μM,(15 min). The reaction was terminated by reduction of pH through addition of citric acid and centrifugation (10 min, $400 \times$ g, 4° C.). Cell viability was monitored before and after experiments using trypan blue exclusion. The cell-free media was decanted and stored at −70° C. until analyzed. Prostaglandin $E_2$ and $LTC_4$ were directly measured in cell-free media using enzyme immunoassay (EIA) kits purchased from Caymen Chemical Co. (Ann Arbor, Mich.). Sample or standard dilutions were made with appropriate media and analyzed in triplicate. Results were obtained by extrapolation from a standard curve prepared in the media and expressed as pg or ng/ml of sample.

Representative compounds of Formula (I) herein which demonstrated positive activity in this assay are:

2-[2-[3-[3,5-Bis(trifluoromethyl)phenyl]ureido]phenoxy]benzoic acid for which demonstrated an $IC_{50}$ of $PGE_2$ 0.1–1 μM and for $LTC_4$—approx 1 μM;

2-[2-[3-(4-Bromophenyl)ureido]-4-trifluoromethyl-phenoxy]benzoic acid which demonstrated an IC$_{50}$ for PGE$_2$ of greater than 3 μM and for LTC$_4$—0.3 μM;

2-2-[2-[3-[3,5-Bis(trifluoromethyl)phenyl]ureido]-4-tri-fluoro-methylphenoxy]benzoic acid which demonstrated an IC$_{50}$ of PGE$_2$ was greater than 10 μM and for LTC$_4$—1-2 μM;

[2-[3-(Octyl)ureido]-4-trifluoromethylphenoxy]benzoic acid which demonstrated an IC$_{50}$ for PGE$_2$ of about −67 @ 3 μM and for LTC$_4$ about −98 @ 3 μM.

In vivo assays

Assays (g and h): Assay (Method) for TPA (assay g) or Arachidonic acid (assay h)-induced Inflammation Animals Male Balb/c inbred mice were obtained from Charle River Breeding Laboratories (Kingston, N.Y.). Within a single experiment mice (22–25 g) were age-matched. These in vivo experiments typically involved use of 5–6 animals/group.

(g) TPA-induced Mouse Ear Inflammation:

Assay of Ear-Edema

TPA (12-0-tetradecanoylphorbol 13-acetate) (Sigma Chemical Company) in acetone (4 mg/20ml) was applied to the inner and outer surfaces of the left ear of BALB/c male mice. The thickness of both ears was then measured with a dial micrometer (Mitutoyo, Japan) at both 2 and 4 hours after treatment, and the data expressed as the change in thickness ($10^{-3}$ cm) between treated and untreated ears. The application of acetone did not cause an edematous response; therefore, the difference in ear thickness represented the response to the TPA. After measuring the edema, the inflammed left ears were removed and stored at −70° C. until they were assayed for MPO (myeloperoxidase) activity where appropriate.

Assay of Myeloperoxidase (MPO) in Inflamed Ear Tissue

On the day of the assay, partially thawed ear tissues were minced and then homogenized (10% w/v) with a Tissumizer homogenizer (Tekmar Co.) in 50 mM phosphate buffer (pH 6) containing 0.5% HTAB. The tissue homogenates were taken through three cycles of freeze-thaw, followed by brief sonication (10 sec). The method of Bradley et al. was used with modifications as described. The appearance of a colored product from the MPO-dependent reaction of o-dianisidine (0.167 mg/ml; Sigma) and hydrogen peroxide (0.0005%; Sigma) was measured spectrophotometrically at 460 nm. Supernatant MPO activity was quantified kinetically (change in absorbance measured over 3 min, sampled at 15-sec intervals) using a Beckman DU-7 spectrophotometer and a Kinetics Analysis package (Beckman Instruments, Inc.). One unit of MPO activity is defined as that degrading one micromole of peroxide per minute at 25° C.

Statistics

Statistical analysis was done using Student's "t" test. The ED$_{50}$ are values which cause a 50% inhibition of the inflammatory response and are calculated by regression analysis of the dose response data.

(h) Arachidonic acid induced car inflammation assay

Arachidonic acid is dissolved in acetone (1 mg/ear) to the left ear of BALB/c male mice. The thickness of both ears was measured with a constant pressure thickness guage 1 hour after treatment and the data expressed as the change in thickness between treated and untreated ears. Test compounds or vehicle are given at the time of AA applciation. The inflammatory cell infiltration is measured by MPO activity as described above in the TPA ear edema assay. After the edema measurements are made, the inflamed ears are removed and assayed for MPO activity.

The anti-inflammatory effect of various standard inhibitors topically administered in the AA and TPA induced mouse ear edema model were measured for dexamethasone, scalaradial and Wyeth's compound WY 50,295 at does of 0.2, 0.1 and 0.3 respectively. The TPA % change in edema was −50 ($p<0.001$), −46 ($p<0.01$) and −18 (ns) respectively; for AA the change was −10 (ns), −11 (ns) and −50 ($p<0.001$). The change in MPO for TPA model was −54 ($p<0.001$), −65 ($p<0.001$) and −36 ($p<0.05$) respectively; for AA it was 0 (ns), −33 (ns) and −90 ($p<0.001$). One hypothesis is that the AA administration to the ear overrides the need for PLA$_2$ mediated liberation of substrate for subsequent proinflammatory lipid mediator generation or AA moblization by CoA-IT. In this case an inhibitor of an AA-metabolizing enzyme should be effective while and inhibitor of PLA$_2$ would be ineffective. As noted above, scalaradial and dexamethasone have little or no effect in the AA ear model at concentrations which were effective in the TPA ear model. This can be contrasted to the activity of the selective 5-LO inhibitor WY 50,295 which strongly inhibits inflammation in response to AA. The AA ear model therefore responds well to compounds that exhibit 5-LO inhibitory action and appears to be uneffected by putative PLA$_2$ inhibitors. This model therefore provides a unique tool with which the contribution of the 5-LO inhibition to the in vivo anti-inflammatory activity of various compounds can be separated from LMW-PLA$_2$ inhibition.

The represesive compounds of Formula (I), 2-[2-[3-[3,5-Bis(trifluoromethyl)phenyl]ureido]phenoxy]benzoic acid, and 2-[2-[3-[3,5-Bis(trifluoromethyl)phenyl]ureido]-4-trifluoro-methylphenoxy]benzoic acid demonstrated a positive inhibition in this animal model. The positive activity of compounds of Formula (I) in this animal model demonstrate a clear utility in the treatment of topically administered diseases associated with inflammation as noted herein such as, but not limited to, inflammatory bowel disease, contact dermatoses, actinic keratosis, psoriasis, or conjunctivitis.

As used herein, various abbreviations and explanations are as follows: [$^3$H], a molecule that contains tritium atoms, a radioactive isotope; A23187, a compound that allows free entry of calcium into a cell; AA, arachidonic acid; arachidonate, arachidonic acid contained within a phospholipid; free arachidonic acid, arachidonic acid that is not contained within a phospholipid; [$^2$H$_8$]arachidonic acid, the form of arachidonic acid labeled with 8 deuterium atoms, a stable isotope; 1-alkyl, 1-O-alkyl; 1-alkenyl, 1-O-alk-1'-enyl; BSA, bovine serum albumin; CoA, coenzyme A; CoA-IT, CoA-independent transacylase; DTT, dithiothreitol; EGTA, [ethylenebis(oxyethylenenitrilo)]tetra acetic acid, a calcium chelator; GPC, sn-glycero-3-phosphocholine; EDTA, a metal ion chelator; GPE, sn-glycero-3-phosphoethanolamine; GC/MS, gas chromatography and mass spectrometry; 5HETE, 5(S)-hydroxyeicosa-6,8,11,14-tetraenoic acid; 15HETE, 15(S)-hydroxyeicosa-5,8,11,13-tetraenoic acid; HL-60, American Type Tissue Culture designated cell line similar to a monocyte; LTB$_4$, leukotriene B$_4$; LTC$_4$, leukotriene C$_4$; LTD$_4$, leukotriene D$_4$; lyso PAF, 1-alkyl-2-lyso-GPC, lyso platelet-activating factor; PLA2, phospholipase A2; PBS, phosphate buffered saline; PAF, platelet activating factor, 1-alkyl-2-acetyl-GPC; PL, phospholipid; PC, phosphatidylcholine; PE, phosphatidylethanolamine, PI, phosphatidylinositol; PMN, polymorphonuclear neutrophilic cell, neutrophil; PS phosphatidylserine; Rf, the distance a compound travels as a fraction of the solvent front; TLC, thin layer chromatography; U937, American Type Tissue Culture designated cell line similar to a monocyte.

The above description fully discloses the invention including preferred embodiments thereof. Modifications and improvements of the embodiments specifically disclosed herein are within the scope of the following claims. Without further elaboration, it is believed that one skilled in the at can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:
1. A compound of the formula:

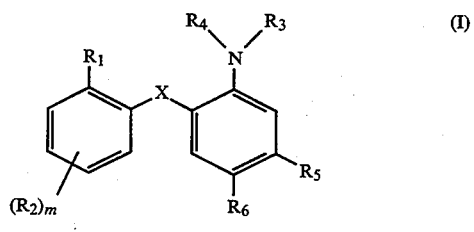

wherein
$R_1$ is $(CH_2)_nOH$ or $(CH_2)_nCO_2R_8$;
n is 0 or an integer having a value of 1;
X is oxygen or sulfur;
$R_2$ is hydrogen, halogen, optionally substituted $C_{1-8}$ alkyl, or $C_{1-8}$ alkoxy;
m is an integer having a value of 1 or 2;
$R_3$ is $C(O)R_7$;
$R_4$ is hydrogen, or $C_{1-4}$ alkyl;
$R_5$ is hydrogen, halogen, $CF_3$, $CH_3$, $(CH_2)_tC(O)_2R_9$, or $(CH_2)_tOH$;
t is 0 or an integer having a value of 1 or 2;
$R_6$ is hydrogen or halogen;
$R_7$ is $NR_9R_{10}$;
$R_8$ is hydrogen or $C_{1-4}$ alkyl;
$R_9$ is hydrogen or $C_{1-4}$ alkyl;
$R_{10}$ is hydrogen, optionally substituted aryl, optionally substituted aryl$C_{1-2}$ alkyl, optionally substituted $C_{1-8}$ alkyl, or together $R_9$ and $R_{10}$ with the nitrogen to which they are attached form a 5 to 7 membered saturated or unsaturated ring which may optionally comprise an additional heteroatom selected from O/N or sulfur;
or a pharmaceutically acceptable salt thereof.

2. The compound according to claim 1 wherein $R_1$ is $(CH_2)_nCO_2R_8$.

3. The compound according to claim 2 wherein $R_{10}$ is an optionally substituted aryl.

4. The compound according to claim 2 wherein the aryl is optionally substituted one to two times by halogen or trifluromethyl.

5. The compound according to claim 3 wherein $R_9$ is hydrogen.

6. The compound according to claim 1 wherein X is oxygen.

7. The compound according to claim 1 wherein $R_2$ is hydrogen, halogen, or optionally substituted $C_{1-8}$ alkyl.

8. The compound according to claim 1 wherein $R_4$ is hydrogen.

9. The compound according to claim 1 wherein $R_5$ is hydrogen, halogen, or $CF_3$.

10. The compound according to claim 1 which is
2-[2-[3-[3,5-Bis(trifluoromethyl)phenyl]ureido]-4-trifluoro-methylphenoxy]benzoic acid;
Methyl 2-[2-[3-[3,5-bis(Trifluoromethyl)phenyl]ureido]-4-trifluoromethylphenoxy]benzoate;
2-[2-[3-[3,5-Bis(trifluoromethyl)phenyl]ureido]phenoxy]benzoic acid;
2-[2-[3-[3,5-Bis(trifluoromethyl)phenyl]ureido]-4-(trifluoromethyl)-phenoxy]-5-(1,1,3,3-tetramethylbutyl)benzoic acid;
2-[2-[3-(4-Bromophenyl)ureido]-4-trifluoromethylphenoxy]benzoic acid;
2-[2-[3-[3,5-bis(trifluoromethyl)phenyl]ureido]-4-trifluoromethyl-phenoxy]-5-(1,1-dimethylpropyl)-benzoic acid;
2-[2-[3-(Octyl)ureido]phenoxy]benzoic acid;
2-[2-[3-(Octyl)ureido]-4-trifluoromethylphenoxy]benzoic acid;
2-[2-[3-[3,5-Bis(trifluoromethyl)phenyl]ureido-4-trifluoromethyl-phenoxy]-4-methoxybenzoic acid;
2-[2-[3-(4-Chlorophenyl)ureido]phenoxy]benzoic acid;
2-[2-[3-[4-Chloro-3-(trifluoromethyl)phenyl]ureido]phenoxy]benzoic acid.

11. A pharmaceutical composition comprising a pharmaceutically acceptable diluent or carrier and a compound according to claim 1.

12. A method for treating or reducing inflammation in a mammal in need thereof which method comprises administering to said mammal an effective amount of a compound according to claim 1.

* * * * *